United States Patent
Tang et al.

(10) Patent No.: US 11,529,392 B2
(45) Date of Patent: *Dec. 20, 2022

(54) CARRIER-FREE BIOLOGICALLY-ACTIVE PROTEIN NANOSTRUCTURES

(71) Applicant: MASSACHUSETTS INSTITUTE OF TECHNOLOGY, Cambridge, MA (US)

(72) Inventors: Li Tang, Quincy, MA (US); Darrell J. Irvine, Arlington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/795,286

(22) Filed: Feb. 19, 2020

(65) Prior Publication Data

US 2020/0360482 A1   Nov. 19, 2020

Related U.S. Application Data

(63) Continuation of application No. 16/451,996, filed on Jun. 25, 2019, now Pat. No. 10,588,942, which is a continuation of application No. 16/195,128, filed on Nov. 19, 2018, now Pat. No. 10,357,544, which is a continuation of application No. 15/470,169, filed on Mar. 27, 2017, now Pat. No. 10,226,510, which is a continuation of application No. 14/498,386, filed on Sep. 26, 2014, now Pat. No. 9,603,944.

(60) Provisional application No. 61/883,503, filed on Sep. 27, 2013.

(51) Int. Cl.
| | |
|---|---|
| *A61K 38/20* | (2006.01) |
| *A61K 47/54* | (2017.01) |
| *A61K 47/68* | (2017.01) |
| *A61K 47/69* | (2017.01) |
| *A61K 47/60* | (2017.01) |

(52) U.S. Cl.
CPC ...... *A61K 38/2013* (2013.01); *A61K 38/2086* (2013.01); *A61K 47/54* (2017.08); *A61K 47/60* (2017.08); *A61K 47/6813* (2017.08); *A61K 47/6835* (2017.08); *A61K 47/6903* (2017.08); *C07K 2319/30* (2013.01); *Y10T 428/2982* (2015.01)

(58) Field of Classification Search
CPC ............ A61K 38/2013; A61K 38/2086; A61K 47/54; A61K 47/60; A61K 47/6813; A61K 47/6835; A61K 47/6903; A61P 35/00; A61P 37/06; A61P 3/10; A61P 9/00; C07K 2319/30; G01C 21/32; G01C 21/3819; G01C 21/3837; H01M 2008/147; H01M 2300/0051; H01M 8/0271; Y02E 60/50; Y10T 428/2982
See application file for complete search history.

(56) References Cited

U.S. PATENT DOCUMENTS

| | | |
|---|---|---|
| 5,409,698 A | 4/1995 | Anderson et al. |
| 5,453,491 A | 9/1995 | Takatsu et al. |
| 5,464,629 A | 11/1995 | Monshipour et al. |
| 5,753,261 A | 5/1998 | Fernandez et al. |
| 5,773,006 A | 6/1998 | Anderson et al. |
| 6,117,982 A | 9/2000 | Chang |
| 6,120,751 A | 9/2000 | Unger |
| 6,194,388 B1 | 2/2001 | Krieg et al. |
| 6,197,298 B1 | 3/2001 | Chang |
| 6,319,715 B1 | 11/2001 | Luo et al. |
| 6,544,549 B1 | 4/2003 | Boni et al. |
| 6,693,086 B1 | 2/2004 | Dow et al. |
| 6,787,132 B1 | 9/2004 | Gabizon et al. |
| 7,108,863 B2 | 9/2006 | Zalipsky et al. |
| 7,122,202 B2 | 10/2006 | Allen et al. |
| 7,223,544 B2 | 5/2007 | Luo et al. |
| 7,402,431 B2 | 7/2008 | Har-Noy |
| 8,192,485 B2 | 6/2012 | Ravi |
| 8,367,051 B2 * | 2/2013 | Matyjaszewski ..... C08F 283/00 424/78.31 |
| 8,747,869 B2 | 6/2014 | Irvine et al. |
| 8,951,542 B2 | 2/2015 | Irvine et al. |
| 9,090,640 B2 * | 7/2015 | Bierbach ................ A61K 45/06 |
| 9,149,432 B2 | 10/2015 | Irvine et al. |
| 9,149,535 B2 | 10/2015 | Xu et al. |
| 9,283,184 B2 | 3/2016 | Irvine et al. |
| 9,339,462 B2 | 5/2016 | Irvine et al. |
| 9,393,199 B2 | 7/2016 | Irvine et al. |

(Continued)

FOREIGN PATENT DOCUMENTS

| | | |
|---|---|---|
| JP | H3-244601 A | 10/1991 |
| JP | 2009-149526 A | 7/2009 |

(Continued)

OTHER PUBLICATIONS

Rodrigues et al. Immunomodulatory Effects of Glutathione, Garlic Derivatives, and Hydrogen Sulfide. Nutrients. 2019, vol. 11, No. 295, pp. 1-21. (Year: 2019).*
Hedge, M. et al., "Tandem CAR T cells targeting HER2 and IL13Ra2 mitigate tumor antigen escape," J Clin Invest., vol. 126(8):3036-3052 (2016).
Kochenderfer, J. et al., "Adoptive transfer of syngeneic T cells transduced with a chimeric antigen receptor that recognizes murine CD19 can eradicate lymphoma and normal B cells," Blood, vol. 116 (19): 3875-3886 (2010).

(Continued)

*Primary Examiner* — Marcela M Cordero Garcia
(74) *Attorney, Agent, or Firm* — McCarter & English, LLP; Jill Ann Mello

(57) ABSTRACT

The present disclosure provides compositions and methods for efficient and effective protein delivery in vitro and in vivo. In some aspects, proteins are reversibly crosslinked to each other and/or modified with functional groups and protected from protease degradation by a polymer-based or silica-based nanoshell.

40 Claims, 23 Drawing Sheets

(56) References Cited

U.S. PATENT DOCUMENTS

| | | |
|---|---|---|
| 9,445,994 B2 | 9/2016 | Irvine et al. |
| 9,603,944 B2* | 3/2017 | Tang .................. A61P 3/10 |
| 9,616,020 B2 | 4/2017 | Irvine et al. |
| 9,750,803 B2 | 9/2017 | Irvine et al. |
| 9,907,753 B2 | 3/2018 | Irvine et al. |
| 10,226,510 B2* | 3/2019 | Tang .................. A61K 38/2013 |
| 10,357,544 B2* | 7/2019 | Tang .................. A61K 38/2013 |
| 10,588,942 B2* | 3/2020 | Tang .................. A61P 9/00 |
| 11,034,752 B2 | 6/2021 | Irvine et al. |
| 11,261,226 B2* | 3/2022 | Irvine .................. A61K 9/127 |
| 2001/0038859 A1 | 11/2001 | Maskiewicz et al. |
| 2001/0043929 A1 | 11/2001 | Zalipsky et al. |
| 2002/0151004 A1 | 10/2002 | Craig |
| 2003/0054027 A1 | 3/2003 | Unger |
| 2003/0235619 A1 | 12/2003 | Allen et al. |
| 2004/0247624 A1 | 12/2004 | Unger et al. |
| 2005/0042298 A1 | 2/2005 | Pardridge et al. |
| 2005/0130180 A1 | 6/2005 | Luo et al. |
| 2005/0214274 A1 | 9/2005 | Har-Noy |
| 2005/0266067 A1 | 12/2005 | Sengupta et al. |
| 2006/0046967 A1 | 3/2006 | Satyam |
| 2006/0263857 A1 | 11/2006 | Lefrancois et al. |
| 2006/0270030 A1 | 11/2006 | Voigt et al. |
| 2006/0275371 A1 | 12/2006 | Dai et al. |
| 2007/0059318 A1 | 3/2007 | Balu-Iyer et al. |
| 2007/0148246 A1 | 6/2007 | Luo et al. |
| 2007/0298093 A1 | 12/2007 | Konur et al. |
| 2008/0014144 A1 | 1/2008 | Saltzman et al. |
| 2008/0267986 A1 | 10/2008 | Pfeifer et al. |
| 2008/0279836 A1 | 11/2008 | Har-Noy |
| 2010/0226973 A1 | 9/2010 | Fujii et al. |
| 2010/0255499 A1 | 10/2010 | Wender et al. |
| 2010/0323018 A1 | 12/2010 | Irvine et al. |
| 2010/0324124 A1 | 12/2010 | Irvine et al. |
| 2011/0020388 A1 | 1/2011 | Zepp et al. |
| 2011/0177156 A1 | 7/2011 | Szoka, Jr. et al. |
| 2011/0206740 A1 | 8/2011 | Karp et al. |
| 2011/0229529 A1 | 9/2011 | Irvine et al. |
| 2011/0229556 A1 | 9/2011 | Irvine et al. |
| 2011/0293705 A1 | 12/2011 | Irvine et al. |
| 2012/0003295 A1 | 1/2012 | Jiang et al. |
| 2012/0121688 A1 | 5/2012 | Ishii et al. |
| 2012/0177724 A1 | 7/2012 | Irvine et al. |
| 2013/0203675 A1 | 8/2013 | DeSimone et al. |
| 2013/0302257 A1 | 11/2013 | Minko et al. |
| 2013/0337471 A1 | 12/2013 | Nie et al. |
| 2014/0017170 A1 | 1/2014 | Irvine et al. |
| 2014/0134128 A1 | 5/2014 | Wong et al. |
| 2014/0377334 A1 | 12/2014 | Irvine et al. |
| 2015/0110740 A1 | 4/2015 | Tang et al. |
| 2015/0272884 A1 | 10/2015 | Irvine et al. |
| 2016/0030304 A1 | 2/2016 | Nagamatsu et al. |
| 2016/0038415 A1 | 2/2016 | Irvine et al. |
| 2016/0256386 A1 | 9/2016 | Irvine et al. |
| 2016/0303046 A1 | 10/2016 | Irvine et al. |
| 2016/0375149 A1 | 12/2016 | Irvine et al. |
| 2017/0049882 A1 | 2/2017 | Irvine et al. |
| 2017/0080104 A1 | 3/2017 | Irvine et al. |
| 2017/0196938 A1 | 7/2017 | Tang et al. |
| 2017/0266114 A1 | 9/2017 | Irvine et al. |
| 2018/0110733 A1 | 4/2018 | Irvine et al. |
| 2018/0185473 A1 | 7/2018 | Irvine et al. |
| 2019/0083576 A1 | 3/2019 | Tang et al. |
| 2020/0001623 A1 | 1/2020 | Tang et al. |
| 2020/0016238 A1 | 1/2020 | Tang et al. |
| 2021/0259968 A1 | 8/2021 | Irvine et al. |
| 2021/0269500 A1 | 9/2021 | Irvine et al. |
| 2022/0185860 A1* | 6/2022 | Irvine .................. C07K 16/2845 |
| 2022/0251160 A1 | 8/2022 | Irvine et al. |

FOREIGN PATENT DOCUMENTS

| | | |
|---|---|---|
| JP | 2013-511539 A | 4/2013 |
| JP | 2013-173689 A | 9/2013 |
| WO | 2004/032970 A2 | 4/2004 |
| WO | 2007/034479 A2 | 3/2007 |
| WO | 2010/059253 A2 | 5/2010 |
| WO | 2010/104865 A2 | 9/2010 |
| WO | 2010/147655 A2 | 12/2010 |
| WO | 2011/063156 A2 | 5/2011 |
| WO | 2012/040323 A2 | 3/2012 |
| WO | 2012/112689 A1 | 8/2012 |
| WO | 2012/142410 A2 | 10/2012 |
| WO | 2015/048498 A2 | 4/2015 |
| WO | 2017/218533 A1 | 12/2017 |

OTHER PUBLICATIONS

Petros, R. et al., "Strategies in the design of nanoparticles for therapeutic applications," Na-ture Reviews, vol. 9: 615-627(2010).

Singh, S. et al., "Embedding of Active Proteins and Living Cells in Redox-Sensitive Hydro-gels and Nanogels through Enzymatic Cross-Linking," Angew. Chem. tnt Ed., vol. 52: 3000-3003 (2013).

Tzeng, A. et al., "Antigen specificity can be irrelevant to immunocytokine efficacy and biodistribution," PNAS, vol. 112 (11): 3320-3325 (2015).

Walter, R. et al., "Simultaneously targeting CD45 significantly increases cytotoxicity of the anti-CD33 immunoconjugate, gemtuzumab ozogamicin, against acute myeloid leukemia (AML) cells and improves survival of mice bearing human AML xenografts," Blood, vol. 111(9):4813-4816 (2008).

Westwood, J.et al., "Toll-Like Receptor Triggering and T-Cell Costimulation Induce Potent Antitumor Immunity in Mice," CCR, vol. 15(24):7624-7633 (2009).

Tang L et al., "Abstract 2792: Engineering T lymphocytes with protein nanogels for cancer immunotherapy," Proceedings of the 105th Annual Meeting of the American Association for Cancer Research; Apr. 5-9, 2014; San Diego, CA Philadelphia (PA): AACR; Cancer Res., 74(19 Suppl):Abstract nr 2792 (2014) doi:10.1158/1538-7445.AM2014-2792.

Tang, L. et al., "Enhancing T cell therapy through TCR-signaling-responsive nanoparticle drug delivery," Nature Biotechnology, Jul. 9, 2018 (Jul. 9, 2018), XP055564253,New York ISSN: 1087-0156, DOI: 10.1038/nbt.4181.

Tangney, M. et al., "The use of Listeria monocytogenes as a DNA delivery vector for cancer gene therapy," Bioeng Bugs., vol. 1 (4):284-287 (2010).

Topalian, S. et al., "Safety, activity, and immune correlates of anti-PD-I antibody in cancer," N Engl. J Med., vol. 366 (26):2443-2454 (2012).

Topalian, SL., et al., "Expansion of human tumor infiltrating lymphocytes for use in immunotherapy trials," J. Immunol. Methods., vol. 102(1): 127-141: (1987) abstract only.

Torchilin, "Recent advances with liposomes as pharmaceutical carriers," Nat Rev Drug Disc., vol. 4(2): 145-160 (2005).

Tosatto, S.C., et al., "Large-scale prediction of protein structure and function from sequence," Current Pharmaceutical Design, vol. 12:2067-2086 (2006).

Trevaskis, NL et al., "Targeted drug delivery to lymphocytes: a route to site-specific immunomodulation," Mol Pharm. vol. 7(6):2297-2309 (2010).

Tsai, S. et al., "Reversal of autoimmunity by boosting memory-like autoregulatory T cells," Immunity, vol. 32 (4):568-580 (2010).

Um et al., "Enzyme-catalysed assembly of DNA hydrogel," Nat Mater.vol. 5(10):797-801 (2006).

Van Broekhoven et al., "The novel chelator lipid 3(nitrilotriacetic acid)-ditetradecylamine (NT A(3)-DTDA) promotes stable binding of His-tagged proteins to liposomal membranes: potent anti-tumor responses induced by simultaneously targeting antigen, cytokine and costimulatory signals to T cells," Biochim Biophys Acta., vol. 1716 (2):104-116 (2006).

Vancha, A. et al., "Use of Polyethyleneimine polymer in cell culture as attachment factor and lipofection enhancer," BMC Biotechnology, vol. 4 (23): 12 pages (2004).

Vangala et al., "Comparison of vesicle based antigen delivery systems for delivery of hepatitis B surface antigen," J Controlled Release, vol. 119(1):102-110 (2007).

(56) References Cited

OTHER PUBLICATIONS

Vasir et al., "Biodegradable nanoparticles for cytosolic delivery of therapeutics," Adv Drug Deliv Rev. vol. 59 (8):718-728 (2007).
Verma et al., "Surface-structure-regulated cell-membrane penetration by monolayer-protected nanoparticles," Nat Mater., vol. 7(7):588-595 (2008).
Von Maltzahn et al., "In vivo tumor cell targeting with click nanoparticles," Bioconjug Chem., vol. 19(8):1570-1578 (2008).
Vonarbourg et al., "Parameters influencing the stealthiness of colloidal drug delivery systems," Biomaterials, vol. 27(24):4356-4373 (2006).
Vugmeyster, Y. et al., "Pharmacokinetic, biodistribution, and biophysical profiles of TNF nanobodies conjugated to linear or branched poly(ethylene glycol)," Bioconjugate Chemistry, vol. 23(7):1452-1462 (2012).
Wakita, D. et al., "An indispensable role of type-1 IFN s for inducing CTL-mediated complete eradication of established tumor tissue by CpG-liposome co-encapsulated with model tumor antigen," Int Immunol., vol. 18(3):425-434 (2006).
Wang, X. et al., "A transgene-encoded cell surface polypeptide for selection, in vivo tracking, and ablation of engineered cells," Blood, vol. 118(5):1255-1263 (2011).
Weinstein et al., "Antibody-mediated targeting of liposomes: Binding to lymphocytes does not ensure incorporation of vesicle contents into the cells," Biochem Biophys Acta., vol. 509(2):272-288 (1978).
Westwood, J.et al., "Three agonist antibodies in combination with high-dose IL-2 eradicate orthotopic kidney cancer in mice," Journal of Translational Medicine, vol. 8(42):1-8 (2010).
Wilson-Welder et al., "Vaccine adjuvants: current challenges and future approaches," J Pharm Sci., vol. 98(4):1278-1316 (2008).
Xing et al.., "Disulfide Core Cross-Linked PEGylated Polypeptide Nanogel Prepared by a One-Step Ring Opening Copolymerization of N-Carboxyandhydrides for Drug Delivery," Macromoleuclar Journals , vol. 11: 962-969 (2011).
Xu J I Ng et al: Il Renderi ng protei n-based; particles transiently insoluble for; therapeutic applications..; Journal of the American Chemical Society; May 30, 2012,; vol. 134, No. 21, May 30, 2012 (May 30, 2012); , pp. 8774-8777, XP002735224.
Yan et al., A novel intracellular protein delivery platform based on single-protein nanocapsules.; Nat Nanotechnol. Jan. 2010;,5(I):48-53. doi: 1O.1038/nnano.2009.341. Epub Nov. 22, 2009.
Yee et al., "Adoptive T cell therapy using antigen-specific CD8+ T cell clones for the treatment of patients with metastatic melanoma: in vivo persistence, migration, and antitumor effect of transferred T cells," Proc Natl Acad Sci USA., vol. 99(25): 16168-16173 (2002).
Zauner et al., "In vitro uptake of polystyrene microspheres: effect of particle size, cell line and cell density," J Control Release, vol. 71(1):39-51 (2001).
Zhang et al., "Folate-decorated poly(lactide-co-glycolide)-vitamin E TPGS nanoparticles for targeted drug delivery," Biomaterials, vol. 28(10):1889-1899 (2007).
Zhao et al., "Directed cell migration via chemoattractants released from degradable crospheres," Biomaterials, vol. 26(24):5048-5063 (2005).
Zheng et al., "In vivo targeting of adoptively transferred T -cells with antibody- and cytokineconjugated liposomes," J Control Release, vol. 172(2):426-445 (2003).
Zheng, "In vivo Arming of Adoptively Transferred T-cells with Drug-loaded Nanoparticles for Cancer Immunotherapy," BMES. Presentation MIT. Oct. 27, 2012, 18 pages.
Zhu et al., "Stabilization of proteins encapsulated in injectable poly (lactide-co-glycolide)," Nat Biotechnol. vol. 18(1):52-57 (1999).
Extended European Search Report, EP Application No. 14813855, dated Jan. 27, 2017, 7 pages.
Fahmy, T. et al., "A nanoscopic multivalent antigen-presenting carrier for sensitive detection and drug delivery to T cells," Nanomedicine, vol. 3(1):75-85 (2007).
Fahmy, T. et al., "Nanosystems for simultaneous imaging and drug delivery to T cells," AAPS J., vol. 9(2):E171-E180 (2007).
Fifis, T. et al., "Size-Dependent Immunogenicity: Therapeutic and protective properties of nano-vaccines against tumors," J Immunol., vol. 173(5):3148-3154 (2004).
Fischer, H. et al., "Nanotoxicity: the growing need for in vivo study," Current Opin Biotechnol., vol. 18(6):565-571 (2007).
Friede, M. et al., "Induction of immune response against a short synthetic peptide antigen coupled to small neutral liposomes containing monophosphoryl lipid A," Mol Immunol., vol. 30(6):539-547 (1993).
Gabizon, A. et al., "Prolonged circulation time and enhanced accumulation in malignant exudates of doxorubicin encapsulated in polyethylene-glycol coated liposomes," Cancer Res., vol. 54(4):987-992 (1994).
Gao, W. et al., "Treg versus Th17 lymphocyte lineages are cross-regulated by LIF versus IL-6," Cell Cycle, vol. 8(9):1444-1450 (2009).
Gao, X. et al., "Lectin-conjugated PEG-PLA nanoparticles: preparation and brain delivery after intranasal administration," Biomaterials, vol. 27(18):3482-3490 (2006).
Garinot, M. et al., "PEGylated PLGA-based nanoparticles targeting M cells for oral vaccination," J Control Release, vol. 120(3):195-204 (2007).
Green, J. et al., "Combinatorial Modification of Degradable Polymers Enables Transfection of Human Cells Comparable to Adenovirus," Advanced Materials, vol. 19(19):2836-2842 (2007).
Gregoriadis, G. et al., "Liposomes as immunological adjuvants and vaccine carriers," J Control Release, vol. 41(1-2):49-56 (1996).
Gunn, J. et al., "A Multimodal Targeting Nanoparticle for Selectively Labeling T Cells," Small, vol. 4(6):712-715 (2008).
Hamdy, S. et al., "Enhanced antigen-specific primary CD4+ and CD8+ responses by codelivery of ovalbumin and toll-like receptor ligand monophosphoryl lipid A in poly(D,L-lactic-co-glycolic acid) nanoparticles," J Biomed Mater Res A., vol. 81(3):652-662 (2006).
Han, K.-P., et al.,"IL-15:IL-15 receptor alpha superagonist complex: High-level co-expression in recombinant mammalian cells, purification and characterization," Cytokine, vol. 56(3):804-810 (2011).
Heffernan, M. et al., "The stimulation of CD8+ T cells by dendritic cells pulsed with polyketal microparticles containing ion-paired protein antigen and poly(inosinic acid)-poly(cytidylic acid)," Biomaterials, vol. 30(5):910-918 (2009).
Heit, A. et al., "Antigen co-encapsulated with adjuvants efficiently drive protective T cell immunity," Eur J Immunol., vol. 37(8):2063-2074 (2007).
Hodi, F. et al., "Improved survival with ipilimumab in Patients with Metastatic Melanoma," N Engl. J. Med., vol. 363(8):711-723 (2010).
Hori, Y. et al., "Injectable dendritic cell-carrying alginate gels for immunization and immunotherapy," Biomaterials, vol. 29(27):3671-3682 (2008).
Hori, T. et al., "Engulfing tumors with synthetic extracellular matrices for cancer immunotherapy," Biomaterials, vol. 30(35):6757-6767 (2009).
Hoiz, J. et al., "Vesicle-templated polymer hollow spheres," Langmuir, vol. 14(5): 1031-1036 (1998).
Hsu, C. et al., "Cytokine-independent growth and clonal expansion of a primary human CD8+ T-cell clone following retroviral transduction with the IL-15 gene," Blood, vol. 109(12):5168-5177 (2007).
Hu, Y. et al., "Cytosolic delivery of membrane-impermeable molecules in dendritic cells using pH-responsive core-shell nanoparticles," Nano Lett., vol. 7(10):3056-3064 (2007).
Immordino, M. et al., "Stealth liposomes: review of the basic science, rationale, and clinical applications, existing and potential," Int J Nanomedicine, vol. 1(3):297-315 (2006).
Internation Preliminary Report on Patentability, PCT/US2014/042004, dated Dec. 22, 2015, 8 pages.
International Preliminary Report on Patentability, PCT/US2009/006290, dated May 24, 2011, 7 pages.
International Preliminary Report on Patentability, PCT/US2014/057789, dated Mar. 29, 2016,12 pages.
International Preliminary Report on Patentability, PCT/US2016/046891, dated Feb. 13, 2018, 6 pages.
International Search Report and Written Opinion, PCT/US2009/006290, dated Aug. 17, 2010, 10 pages.

(56) References Cited

OTHER PUBLICATIONS

International Search Report and Written Opinion, PCT/US2014/042004, dated Nov. 3, 2014, 10 pages.
International Search Report and Written Opinion, PCT/US2014/057789, dated Jan. 6, 2015, 17 pages.
International Search Report and Written Opinion, PCT/US2016/046891, dated Oct. 31, 2016, 8 pages.
Irvine, D.J. "Engineering nanomaterials as vaccine adjuvants and agents for cancer immunotherapy," Seminar at Scripps Res Institute, Apr. 28, 2011, 57 slides.
Irvine, D.J. "Engineering nanoparticle delivery for vaccines and immunotherapy," Nanotechnology in Infectious Disease Meeting, Atlanta, GA , 33 pages (2010).
Irvine, D.J. et al., "Combining cell therapy with nanotechnology for enhanced cancer immunotherapy," 16th International Symposium on Recent Advances in Drug Delivery Systems, Salt Lake City, UT., Feb. 3-6, Abstract, 2 pages (2013).
Jain, N. et al., "Targeted drug delivery to macrophages," Expert Opin Drug Deliv., vol. 10(3):353-367 (2013).
Jeong, J. et al., "Enhanced adjuvantic property of polymerized liposome as compared to a phospholipid liposome," J Biotechnol., vol. 94(3):255-263 (2002).
Jiang, W. et al., "Biodegradable poly(lactic-co-glycolic acid) microparticles for injectable delivery of vaccine antigens," Adv Drug Deliv Rev., vol. 57(3):391-410 (2005).
Johnson, RM., "The kinetics of Resealing of Washed Erythricyte Ghosts," J. Membr. Biol., vol. 22 (3-4):231-251 (1975).
Jones et al., "Releasable luciferin-transporter conjugates: tools for the real-time analysis of cellular uptake and release," J Am Chem. Soc., vol. 128(20):6526-6527 (2006).
Jones, DT "Critically assessing the state-of-the-art in protein structure prediction," Pharmacogenomics Journal, vol. 1(2):126-134 (2001).
June, C. "Principles of adoptive T cell cancer therapy," J Clin Invest., vol. 117(5):1204-1212 (2007).
Kaiser-Schulz, G. et al., "Polylactide-coglycolide microspheres co-encapsulating recombinant tandem prion protein with CpG-oligonucleotide break self-tolerance to prion protein in wild-type mice and induce CD4 and CD8 T cell responses," J Immunol., vol. 179(5):2797-2807 (2007).
Kalos, M. "Biomarkers in T cell therapy clinical trials," J Trans Med., vol. 9(138) 9 pages (2011).
Kalos, M. et al., "T cells with chimeric antigen receptors have potent antitumor effects and can establish memory in patients with advanced leukemia," Sci Trans Med., vol. 3(95), 12 pages (2007).
Kerkar, S. et al., "Tumor-specific CD8+ T cells expressing interleukin-12 eradicate established cancers in lymphodepleted hosts," Cancer Res., vol. 70(17):6725-6734 (2010).
Kirby, C. et al., "Dehydration-rehydration vesicles: a simple method for high yield drug entrapment in liposomes," Nat Biotechnol., vol. 2(11):979-984 (1984).
Kirpotin, D. et al., "Antibody targeting of long-circulating lipidic nanoparticles does not increase tumor localization but does increase internalization in animal models," Cancer Res., vol. 66(13):6732-6740 (2006).
Klebanoff, C. et al., "Sinks, suppressors and antigen presenters: how lymphodepletion enhances T cell-mediated tumor immunotherapy," Trends Immunol., vol. 26(2): 111-117 (2005).
Kobayashi, H. et al., "Phase I/II study of adoptive transfer of γδ T cells in combination with zoledronic acid and IL-2 to patients with advanced renal cell carcinoma," Cancer Immunol. Immunother, vol. 60(8):1075-1084 (2011).
Akagi, T. et al., "Development of Vaccine Adjuvants Using Polymeric Nanoparticles and Their Potential Applications for Anti-HIV Vaccine," Yakugaku Zasshi, vol. 127(2):307-317 (2007).
Akin, D. et al., "Bacteria-mediated delivery of nanoparticles and cargo into cells," Nat Nanotechnol., vol. 2(7):441-449 (2007).
Allen, T. et al., "Anti-CD19-Targeted Liposomal Doxorubicin Improves the Therapeutic Efficacy in Murine B-Cell Lymphoma and Ameliorates the Toxicity of Liposomes with Varying Drug Release Rates," Clin Cancer Res., vol. 11(9):3567-3573 (2005).
Allen, T. et al., "Drug Delivery Systems: Entering the Mainstream. Science," vol. 303(5665): 1818-1822 (2004).
Alving, C., "Liposomes as carriers of antigens and adjuvants," J Immunol Methods. vol. 40(1):11-13 (1991).
Alving,C. "Lipopolysaccharide, Lipid A, and Liposomes Containing Lipid A as Immunologic Adjuvants," Immunobiology, vol. 187(3-5):430-446 (1993).
Babensee, J. et al., "Differential levels of dendritic cell maturation on different biomaterials used in combination products," J Biomed Mater Res A. vol.74(4):503-510. (2005) (Winner of the Young Investigator Award, 30th Ann Mtg Soc Biomater, Memphis, TN, Apr. 27-30, 2005.).
Bal, S. et al., "Efficient induction of immune responses through intradermal vaccination with N-trimethyl chitosan containing antigen formulations," J Control Release,vol. 142(3):374-383 (2010).
Barral, P. et al., "B cell receptor-mediated uptake of CD1d-restricted antigen augments antibody responses by recruiting invariant NKT cell help in vivo," Proc Natl Acad Sci USA, vol. 105(24):8345-8350 (2008).
Baudino, L. et al., "Crucial Role of Aspartic Acid at Position 265 in the CH2 domain for murine IgG2a and IgG2b Fc-Associated effector functions," J Immunol. vol. 181(9):6664-6669 (2008).
Beisiegel, U. et al., "The LDL-receptor-related protein, LRP, is an apolipoprotein E-binding protein," Nature, vol. 341(6328):162-164 (1989).
Bennewitz, N.et al., "The effect of the physical form of poly(lactic-co-glycolic acid) carriers on the humoral immune response to co-delivered antigen," Biomaterials, vol. (16):2991-2999 (2005).
Bershteyn et al., Versatile lipid-based vaccine carriers elicit CTL and antibody responses to surface-conjugated or encapsulated antigen. Keystone Symposium. Poster Presentation. 2010. 1 page.
Bershteyn, A. et al., "Polymer-supported lipid shells, onions, and flowers," Soft Matter, vol. 4(9):1787-1791 (2008).
Bershteyn, A.et al. "Lipid-Coated Nano-and Microparticles for Vaccine Design," Materials Research Society fall meeting, 7 pages (2009).
Bershteyn, A.et al., "Robust IgG responses to nanograms of antigen using a biomimetic lipid-coated particle vaccine," J Control Release, vol. 157(3):354-65 (2012).
Berstheyn, A.et al., "Versatile Lipid-Based Vaccine carriers Elicit CTL and Antibody Responses to Surface-Conjugated or Encapsulated Antigen," Keystone Symposium, Abstract, 1 page (2010).
Besser, M. et al., "Clinical Responses in a Phase II Study Using Adoptive Transfer of Short-term Cultured Tumor in Fillration Lymphocytes in Metastatic Melanoma Patients," Clin Cancer Res., vol. 16(9):2646-2655 (2010).
Bhowmick, S. et al., "Comparison of liposome based antigen delivery systems for protection against Leishmania donovani," J Controlled Release, vol. 141(2):199-207 (2010).
Bottini, M. et al., "Luminescent Silica Nanobeads: Characterization and Evaluation as Efficient Cytoplasmatic Transporters for T-Lymphocytes," JACS, vol. 129(25):7814-7823 (2007).
Brocchini et al., "Disulfide bridge based PEGylation of proteins," Advanced Drug Delivery Reviews,vol. 60: 3-12 (2008).
Cai, Z. et al., "Encapsulated enhanced green fluorescence protein in silica nanoparticle for cellular imaging," Nanoscale, vol. 3(5):1974-1976 (2011).
Cashion, M. et al., "Biomimetic Design and Performance of Polymerizable Lipids," Accounts Chem. Res., vol. 42(8):1016-1025 (2009).
Chacon, M. et al., "Optimized preparation of poly d,l (lactic-glycolic) microspheres and nanoparticles for oral administration," Int J Pharm., vol. 141(1-2):81-91 (1996).
Chambers, E. et al., "Long Circulating Nanoparticles via Adhesion on Red Blood Cells: Mechanism and Extended Circulation," Exp Biol Med (Maywood), vol. 232(7):958-966 (2007).
Chambers, E. et al., "Prolonged circulation of large polymeric nanoparticles by non-covalent adsorption on erythrocytes," J Control Release, vol. 100(1): 111-119 (2004).
Chen, L. et al., "Characterization of PLGA microspheres for the controlled delivery of IL-1a for tumor immunotherapy," J Controlled Rel., vol. 43:261-272 (1997).

(56) References Cited

OTHER PUBLICATIONS

Chirifu et al., "Crystal structure of the IL-15-IL-15Ralpha complex, a cytokine-receptor unit presented in trans.," Nature Immunology, vol. 8(9):1001-1007. (2007).
Cho et al., "Understanding the Role of Surface Charges in Cellular Adsorption versus In-ternalization by Selectively Removing Gold Nanoparticles on the Cell Surface with a 1-2/KI Etchant," Nano Lett., 9(3):1080-1084 (2009).
Clemente-Casares, X. et al., "Peptide-MHC-based nanovaccines for the treatment of autoimmunity: a "one size fits all" approach?" J Mol Med., vol. 89(8):733-742 (2011).
Cole, C. et al., "Tumor-targeted, systemic delivery of therapeutic viral vectors using hitchhiking on antigen-specific T cells," Nat Med., vol. 11(10):1073-1081 (2005).
Collins, D. et al., "Processing of exogenous liposome-encapsulated antigens in vivo generates class I MHC-restricted T cell responses," J Immunol., vol. 148(11):3336-3341 (1992).
Coronoa-Ortega, T. et al., "Characterization of cationic liposomes having IL-2 expressed on their external surface, and their affinity to cervical cancer cells expressing the IL-2 receptor," Journal of Drug Targeting, vol. 17(7):496-501 (2009).
Davis, M. et al., "Nanoparticle therapeutics: an emerging treatment modality for cancer," Nat Rev Drug Discov., 7(9):771-782 (2008).
De La Pena, H. et al., "Artificial exosomes as tools for basic and clinical immunology," J Immunol. Methods, vol. 344(2):121-132. (2009).
Demento, S. et al., "Inflammasome-activating nanoparticles as modular systems for optimizing vaccine efficacy," Vaccine, vol. 27(23):3013-3021 (2009).
Dinauer, N. et al., "Selective targeting of antibody-conjugated nanoparticles to leukemic cells and primary T-lymphocytes," Biomaterials, vol. 26(29):5898-5906 (2005).
Ding, H. et al., "Bioconjugated PLGA-4-arm-PEG branched polymeric nanoparticles as novel tumor targeting carriers," Nanotechnology, vol. 22(16): p. 165101 (2011).
Diwan, M. et al., "Dose Sparing of CpG Oligodeoxynucleotide Vaccine Adjuvants by Nanoparticle Delivery," Curr Drug Deliv., vol. 1(4):405-412 (2004).
Dou, H. et al., "Development of a macrophage-based nanoparticle platform for antiretroviral drug delivery," Blood., vol. 108(8):2827-2835 (2006).
Drummond, D. et al., "Optimizing Liposomes for Delivery of Chemotherapeutic Agents to solid tumors," Pharmacol Rev., vol. 51(4):691-743 (1991).
Dubikovska, Y.A ., et al., "Overcoming multidrug resistance of small-molecule therapeutics through conjugation with releasable octaarginine transporters," PNAS USA, vol. 105(34):12128-12133 (2008).
Dudley, M. et al., "A phase I Study of Nonmyeloablative Chemotherapy and Adoptive Transfer of Autologous Tumor Antigen-specific T lymphocytes in patients with Metastatic Melanoma," J Immunother, vol. 25(3):243-251 (2002).
Dudley, M. et al., "Cancer Regression and Autoimmunity in Patients after Clonal Repopulation with Antitumor Lymphocytes," Science, vol. 298(5594):850-854 (2002).
Eck, W. et al., "Anti-CD4-targeted gold nanoparticles induce specific contrast enhancement of peripheral lymph nodes in X-ray computed tomography of live mice," Nano Lett vol. 10(7):2318-2322 (2010).
Edwards, B. et al.,"The Remarkable Flexibility of the Human Antibody Repertoire Isolation of Over One Thousand Different Antibodies to a Single Protein," BLyS, J Mol Biol., vol. 334(1):103-118 (2003).
Elamanchili, P. et al., "Characterization of poly(D,L-lactic-co-glycolic acid) based nanoparticulate system for enhanced delivery of antigens to dendritic cells," Vaccine, vol. 22(19):2406-2412 (2004).
Endsley, A. et al., "Enhanced anti-HIV Efficacy of Indinavir after inclusion in CD4-targeted lipid nanoparticles," J Acquir Immune Defic Syndr., vol. 61(4):417-424 (2012).
European Search Report, EP 09827900, dated Aug. 17, 2015, pp. 1-3.
European Search Report, European Application No. 16836005.5, dated Jun. 19, 2019, 14 pages.
Konigsberg, P.J. "The development of IL-2 conjugated liposomes for therapeutic purposes," Biochimica Biophysica Acta, vol. 1370(2):243-251 (1998).
Konrad, M. et al., "Pharmacokinetics of recombinant interleukin 2 in humans," Cancer Res., vol. 50(7):2009-2017 (1990).
Krishna, N. et al., "Genetic Determinants of Rous Sarcoma Virus Particle Size," Journal of Virology, vol. 72 (1):564-577 (1998).
Kudchodkar, S. et al., "Improving CAR T Cell Efficacy for Solid Tumors By Nanogel-Based Delivery of Immunomodulatory Proteins," Molecular Therapy: The Journal of The American Society of Gene Therapy, vol. 23(SI):S207-S207 (2015).
Kwon, Y. et al., "In vivo targeting of dendritic cells for activation of cellular immunity using vaccine carriers based on pH-responsive microparticles," Proc Natl Acad Sci USA., vol. 102(51):18264-18268 (2005).
Kwong, B. et al., "Localized immunotherapy via liposome-anchored Anti-CD137 + IL-2 prevents lethal toxicity and elicits local and systemic antitumor immunity," Cancer Res., vol. 73(5):1547-1558 (2013).
Kwong, B. et al., "Induction of potent anti-tumor responses while eliminating systemic side effects via liposome-anchored combinatorial immunotherapy," Biomaterials, Elsevier Science Publishers BV, vol. 32(22):5134-5147 (2011).
Kwong, B., "Liposome-anchored local delivery of immunomodulatory agents for tumor therapy," Biological Engineering, Massachusetts Institute of Technology. 2005. Jun. 2012. (175 pages).
Lachman, L. et al., "Cytokine-containing liposomes as vaccine adjuvants," Eur Cytokine Netw., vol. 7(4):693-698 (1996).
Lateef et al., "An Improved Protocol for Coupling Synthetic Peptides to Carrier Proteins for Antibody Production Using DMF to Solubilize Peptides," J. Biomolecular Techniques, vol. 18(3):173-176 (2007).
Lavelle, E.C. et al., "The stability and immunogenicity of a protein antigen encapsulated in biodegradable microparticles based on blends of lactide polymers and polyethylene glycol.," Vaccine, vol. 17(6):512-529 (1999).
Lee, J. et al., "Multifunctional nanoarchitectures from DNA-based ABC monomers," Nat Nanotechnol. vol. 4(7):430-436 (2009).
Leland et al., "Cancer chemotherapy—ribonucleases to the rescue," Chem Biol., vol. 8(5): 405-413 (2001).
Li, J. et al., "Purification of melanoma reactive T cell by using a monocyte-based solid phase T-cell selection system for adoptive therapy," J Immunother., vol. 31(1):81-88 (2008).
Li, Y. et al., "PEGylated PLGA nanoparticles as protein carriers: synthesis, preparation and biodistribution in rats," J Control Release, vol. 71(2):203-211. (2001).
Lloyd, C. et al., "Modelling the human immune response: performance of a 10" human antibody repertoire against a broad panel of therapeutically relevant antigens," Protein Engineering, Design & Selection, vol. 22(3):159-168 (2009).
Lodish, H. et al., "Chemical Foundations," In: Molecular Cell Biology, Fifth Eds. Chapter 2, pp. 29-57 (2004).
Lowenthal, J. et al., "Similarities between interleukin-2 receptor number and affinity on activated B and T lymphocytes," Nature, vol. 315(6021):669-672 (1985).
Lowenthal, J. et al., "High and low affinity IL 2 receptors: analysis by IL 2 dissociation rate and reactivity with monoclonal anti-receptor antibody PC61," J Immunol., vol. 135(6):3988-3994 (1985).
Lu, W. et al., "Cationic albumin-conjugated pegylated nanoparticles as novel drug carrier for brain delivery," J Control Release, vol. 107(3):428-448 (2005).
Lutsiak, M. et al., "Analysis of poly(D,L-lactic-co-glycolic acid) nanosphere uptake by human dendritic cells and macrophages in vitro," Pharm Res., vol. 19(10):1480-1487 (2002).
MacLaughlin, C.M., et al., "Polymer-coated surface enhanced Raman scattering (SERS) gold nanoparticles for multiplexed labeling of chronic lymphocytic leukemia cells," Frontiers in Biological Detection: From Nanosensors to Systems IV, SPIE, vol. 8212(1):1-11 (2012).

(56) References Cited

OTHER PUBLICATIONS

Maeda, H. et al., "Tumor vascular permeability and the EPR effect in macromolecular therapeutics: a review.," J Control Release, vol. 65(1-2):271-284 (2000).
Maloy, K. et al., "Induction of mucosal and systemic immune responses by immunization with ovalbumin entrapped in poly(lactide-co-glycolide) microparticles," Immunology, vol. 81(4):661-667 (1994).
Markley, J. et al., "IL-7 and IL-21 are superior to IL-2 and IL-15 in promoting human T cell-mediated rejection of systemic lymphoma in immunodeficient mice," Blood, vol. 115(17):3508-3519 (2010).
Martinez Gomez, J. et al., "A protective allergy vaccine based on CpG-and protamine-containing PLGA microparticles," Pharm Res., vol. 24(10):1927-1935 (2007).
Matsumoto, N. et al.,"Synthesis of Nanogel-Protein Conjugates," Polym Chem., vol. 4(8): 2464-2469 (2013).
Matsumura, Y. et al., "A new concept for macromolecular therapeutics in cancer chemotherapy: mechanism of tumoritropic accumulation of proteins and the antitumor agent smancs," Cancer Res., vol. 46(12 Pt 1):6387-6392 (1986).
McKee, A. et al., "How do adjuvants work? Important considerations for new generation adjuvants," Immunity, vol. 27(5):687-690 (2007).
Mellman, I. et al., "Cancer immunotherapy comes of age," Nature, vol. 480(7378):480-489 (2011).
Meng, F. et al., "Reduction-sensitive polymers and bioconjugates for biomedical applica-tions," Biomaterials, vol. 30:2180-2198 (2009).
Minami, Y. et al., "The IL-2 receptor complex: its structure, function, and target genes," Annu Rev. Immunol., vol. 11:245-268 (1993).
Moghimi, S. et al., "Long-circulating and target-specific nanoparticles: theory to practice," Pharmacol Rev. vol. 53(2):283-318 (2001).
Mohammed, A. et al., "Lyophilisation and sterilisation of liposomal vaccines to produce stable and sterile products," Methods, vol. 40(1):30-38 (2006).
Moon, J. et al., "Engineering nano-and microparticles to tune immunity," Adv Mater., vol. 24(28):3724-3746 (2012).
Moon, J. et al., "Enhancing humoral responses to a malaria antigen with nanoparticle vaccines that expand Tfh cells and promote germinal center induction," Proc Natl Acad Sci USA., vol. 109(4):1080-1085 (2012).
Moon, J. et al., "Interbilayer-crosslinked multilamellar vesicles as synthetic vaccines for potent humoral and cellular immune responses," Nat Mater., vol. 10(3) 243-251 (2011).
Moore, A. et al., "Tracking the recruitment of diabetogenic CD8+ T-cells to the pancreas in real time," Diabetes, vol. 53(6):1459-1466 (2004).
Morgan, R. et al., "Cancer regression in patients after transfer of genetically engineered lymphocytes," Science, vol. 314(5796):126-129 (2006).
Mortensen, M.W. et al., "Next generation adoptive immunotherapy—human T cells as carriers of therapeutic nanoparticles," J Nanosci Nanotechnol., vol. 7(12):4575-4580 (2007).
Mundargi, R. et al., "Nano/micro technologies for delivering macromolecular therapeutics using poly(D,L-lactide-co-glycolide) and its derivatives," J Control Release., vol. 125(3):193-209 (2008).
Murcia,M. et al., "Design of quantum dot-conjugated lipids for long-term, high-speed tracking experiments on cell surfaces," J Am Chem Soc., vol. 130(45): 15054-15062 (2008).
Murphy, R. et al., "Endosome pH measured in single cells by dual fluorescence flow cytometry: rapid acidification of insulin to pH 6," J Cell Biol., vol. 98(5): 1757-1762 (1984).
Nguyen et al., "Disulfide-crosslinked heparin-pluronic nanogels as redox-sensisitve nanocarrier for intracellular protein delivery," Bioactive and Compatible Polymers, vol. 26 (3): 287-300 (2011).
O'Hagan, D. et al., "Induction of potent immune responses by cationic microparticles with adsorbed human immunodeficiency virus DNA vaccines," J Virol., vol. 75(19):9037-9043 (2001).
O'Hagan, D. et al., "Microparticles as potentially orally active immunological adjuvants," Vaccine, vol. 7(5):421-424 (1989).

O'Hagan, D. et al., "Microparticles as vaccine adjuvants and delivery systems," Expert Rev Vaccines, vol. 2(2):269-283 (2003).
O'Hagan, D. et al., "Poly(lactide-co-glycolide) microparticles for the development of single-dose controlled-release vaccines," Adv Drug Deliv Rev. vol. 32(3):225-246 (1987).
Overwijk, W. et al.,"Tumor regression and autoimmunity after reversal of a functionally tolerant state of self-reactive CD8+ T cells," J Exp Med., vol. 198(4):569-580 (2003).
Owens, D. et al., "Opsonization, biodistribution, and pharmacokinetics of polymeric nanoparticles.," Int J Pharm. , vol. 307(1):93-102 (2006).
English Translation of JP Office Action, JP Appln. No. 2020-109309, dated Sep. 7, 2021, 3 pages.
Igaku-no-Ayumi, 2013, 244(9), 831-836,No English Translation available, cited in corresponding JP Office Action, JP Appln. No. 2020-109309, dated Sep. 7, 2021, 3 pages cited herein.
Kagaku-to-Seibutsu, 1990, 28(1), 62-66, No English Translation available. cited in corresponding JP Office Action, JP Appln. No. 2020-109309, dated Sep. 7, 2021, 3 pages cited herein.
Neville et al., Biopharmaceutics of liposomal interleukin 2, oncolipin. Cytokine. Nov. 2000;12(11):1691-701.
U.S. Appl. No. 17/682,633, filed Feb. 28, 2022, 2022-0185860, Published.
U.S. Appl. No. 15/066,680, filed Mar. 10, 2016, Abandoned.
U.S. Appl. No. 17/522,663, filed Nov. 9, 2021, 2022-0251160, Published.
U.S. Appl. No. 17/069,305, filed Oct. 13, 2020, 2021-0259968, Published.
Park, J. et al., "Anti-HER2 immunoliposomes:enhanced efficacy attributable to targeted delivery," Clin Cancer Res., vol. 8(4):1172-1181 (2002).
Park, J. et al., "Modulation of CD4+ T lymphocyte lineage outcomes with targeted, nanoparticle-mediated cytokine delivery," Mol Pharm., vol. 8(1):143-152 (2011).
Partial European Search Report, European Application No. 16836005.5, dated Mar. 18, 2019, 16 pages.
Paulos, C. et al., "Toll-like receptors in tumor immunotherapy," Clin Cancer Res., vol. 13(18 Pt 1):5280-5289 (2007).
Perche, F. et al., "Recent trends in multifunctional liposomal nanocarriers for enhanced tumor targeting," J Drug Deliv. Article ID. 705265, 32 pages (2013).
Perica, K. et al., "Magnetic field-induced T cell receptor clustering by nanopartides enhances T cell activation and stimulates antitumor activity," ACS Nano., vol. 8(3):2252-2260 (2013).
Phillips, N.et al., "Immunoliposome targeting to murine CD4+ leucocytes is dependent on immune status," J Immunol., vol. 152(6):3168-3174 (1993).
Plunkett et al., "Chymotrypsin Responsive Hydrogel: Application of a Disulfide Exchange Protocol for the Preparation of Methacrylamide Containing Peptides," Biomacromolecules, vol. 6 (2):632-637 (2005).
Popescu, M. et al., "A novel proteoliposomal vaccine elicits potent antitumor immunity in mice," Blood, vol. 109(12):5407-5410 (2007).
Press et al., "Retention of B-Cell-Specific Monoclonal Antibodies by Human Lymphoma Cells," Blood, 83(5):1390-1397 (1994).
Prieto, P. et al., "Enrichment of CD8+ cells from melanoma tumor-infiltrating lymphocyte cultures reveals tumor reactivity for use in adoptive cell therapy," J Immunother., vol. 33(5):547-556 (2010).
Prokop, A. et al., "Hydrogel-based colloidal polymeric system for protein and drug delivery: physical and chemical characterization, permeability control and applications," Advances in Polymer Science, vol. 160:119-173 (2002).
Puri, A. et al., "HER2-specific affibody-conjugated thermosensitive liposomes (Affisomes) for improved delivery of anticancer agents," J Liposome Res., vol. 18(4):293-307 (2008).
Qiao, J. et al., "Purging metastases in lymphoid organs using a combination of antigen-nonspecific adoptive T cell therapy, oncolytic virotherapy and immunotherapy," Nat Med, vol. 14(1):37-44 (2008).
Rangel-Corona, R. et al., "Cationic liposomes bearing IL-2 on their external surface induced mice leukocytes to kill human cervical cancer cells in vitro, and significantly reduced tumor burden in immunodepressed mice," J Drug Target. vol. 19(2):79-85 (2011).

(56) References Cited

OTHER PUBLICATIONS

Reddy, R. et al., "In vivo cytotoxic T lymphocyte induction with soluble proteins administered in liposomes," J Immunol. vol. 148(5):1585-1589 (1992).

Reddy, S. et al., "Exploiting lymphatic transport and complement activation in nanopartide vaccines," Nature Biotechnology, vol. 25(10):1159-1164 (2007).

Reed, S. et al., "New horizons in adjuvants for vaccine development," Trends Immunol., vol. 30(1):23-32 (2009).

Restifo, N. et al., "Adoptive immunotherapy for cancer: harnessing the T cell response," Nat Rev. Immunol., vol. 12(4):269-281(2012).

Ring et al., "Mechanistic and structural insight into the functional dichotomy between IL-2 and IL-15," Nature Immunology, vol. 13 (12):1187-1197 (2012).

Rosenberg, S. et al., "Adoptive cell transfer: a clinical path to effective cancer immunotherapy," Nat Rev Cancer, vol. 8(4):299-308 (2008).

Rubin, B. et al., "Fractionation of T cell subsets on Ig anti-Ig columns: Isolation of helper T cells from nonresponder mice, demonstration of antigen-specific T suppressor cells, and selection of CD-3 negative variants of Jurkat T cells," Cellular Immunology, vol. 119(2):327-340. (1989).

Rubinstein, M. et al., "Converting IL-15 to a superagonist by binding to soluble IL-15R{alpha}," Proc Natl Acad Sci USA., vol. 103(24):9166-9171 (2006).

Rubinstein, M. et al., "Ex vivo interleukin-12-priming during CD8 ( +) T cell activation dramatically improves adoptive T cell transfer antitumor efficacy in a lymphodepleted host," J Am Coll Surg., vol. 24(4):700-707 (2012).

Sahaf, B. et al., "Lymphocyte surface thiol levels," Proc Natl Acad Sci USA., vol. 100(7):4001-4005 (2003).

Schlosser et al., "TLR ligands and antigen need to be coencapsulated into the same biodegradable microsphere for the generation of potent cytotoxic T lymphocyte responses," Vaccine, vol. 26(13):1626-1637 (2008).

Scott et al., "Protein adsorption and cell adhesion on nanoscale bioactive coatings formed from poly(ethylene glycol) and albumin microgels," Biomaterials, vol. 29(34):1-93 (2008).

Seeman, P. et al., "Transient Holes in the Erythrocyte Membrane During Hypotonic Hemolysis and Stable Holes in the Membrane After Lysis By Saponin and Lysolecithin," The Rockefeller University, J Cell Biol., vol. 32(1): 55-70 (1967).

Shi et al., "Dendrimer-functionalized shell-crosslinked iron oxide nanoparticles for in-vivo magnetic resonance imaging of tumors.," Advanced Materials, vol. 20(9): 1671-1678 (2008).

Shilyansky, J. et al., "T-cell receptor usage by melanoma-specific clonal and highly oligoclonal tumor-infiltrating lymphocyte lines," PNAS, vol. 91: 2829-2833 (1994).

Shimizu, T. et al., "Nanogel DDS enables sustained release of IL-12 for tumor immunotherapy," BBRC, vol. 367(2):330-335 (2008).

Singh et al., "Anionic microparticles are a potent delivery system for recombinant antigens from Neisseria meningitidis serotype B," J Pharm Sci., vol. 93(2):273-282 (2003).

Singh et al., "Cationic microparticles are an effective delivery system for immune stimulatory cpG DNA," Pharm Res., vol. 18(10):1476-1479 (2001).

Singh et al., "Cationic micropartides: A potent delivery system for DNA vacdnes," Proc Natl Acad Sci USA., vol. 97(2):811-816 (2007).

Singh et al., "Charged polylactide co-glycolide micropartides as antigen delivery systems," Expert Opin Biol Ther., vol. 4(4):483-491 (2004).

Singh et al., "Immunogenicity and protection in small-animal models with controlled-release tetanus toxoid micropartides as a single-dose vaccine," Infect Immun., vol. 65(5):1716-17121 (2001).

Singh et al., "Nanopartides and microparticles as vaccine-delivery systems," Expert Rev Vaccines, vol. 6(5):797-808 (2007).

Singh et al., "Polylactide-co-glycolide microparticles with surface adsorbed antigens as vaccine delivery systems," Curr Drug Deliv., vol. 3(1):115-120 (2006).

Singh et al., "Recent advances in vaccine adjuvants," Pharm Res., vol. 19(6):715-728 (2002).

Society for Experimental Biology and Medicine, Nanopartides hitchhike on red blood cells for drug delivery. RxPG News. Jun. 27, 2007. Last retrieved from http://www.rxpgnews.com/drugdelivery/Nanopartides-hitchhike-on-red-blood-cells-a-potential-new-method-lor-drug-delivery_40324.shtml on Nov. 8, 2012.

Steers, N. et al.,"Liposome-encapsulated HIV-1 Gag p24 containing lipid A induces effector CD4+ T-cells, memory CD8+ T-cells, and pro-inflammatory cytokines," Vaccine, vol. 27(49):6939-6949 (2009).

Steinfeld, U., et al, "T lymphocytes as potential therapeutic drug carrier for cancer treatment," Int. J. Pharm., vol. 311:229-236 (2006).

Stephan et al., "Enhancing Cell therapies from the Outside In: Cell Surface Engineering Using Synthetic Nanomaterials," Nano Today., vol. 6(3):309-325 (2011).

Stephan et al., "Synapse-direded delivery of immunomodulators using T-cell-conjugated nanopartides," Biomaterials, vol. 33(23):5776-5787 (2012).

Stephan et al., "T cell-encoded CD80 and 4-1BBL induce auto-and transcostimulation, resulting in potent tumor rejection," Nat Med., vol. 13(12): 1440-1449. (2007).

Stephan, M. et al., "Therapeutic cell engineering with surface-conjugated synthetic nanoparticles," Nat Med., vol. 16(9):1035-1041 (2010).

Supplementary European Search Report, EP Application No. 09827900. 3, dated Sep. 10, 2015, 7 pages.

Swiston et al., "Surface functionalization of living cells with multilayer patches," Nano Lett., vol. 8(12):4446-4453 (2008).

Takasaki et al., "Micelles as intermediates in the preparation of protein-liposome conjugates," Bioconjug Chem., vol.17(2):438-450 (2006).

Tan et al., PEG-urokinase nanogels with enhanced stability and controllable bioactivity. Soft; Matter. 2012;8:2644-2650.

\* cited by examiner

|  | IL2-fc-NC | IL2-fc/liposome |
|---|---|---|
| Incorporation efficiency[a] | 95.5% | 0.97% |
| Loading[b] | 84.0% | 0.22% |
FIG. 4A
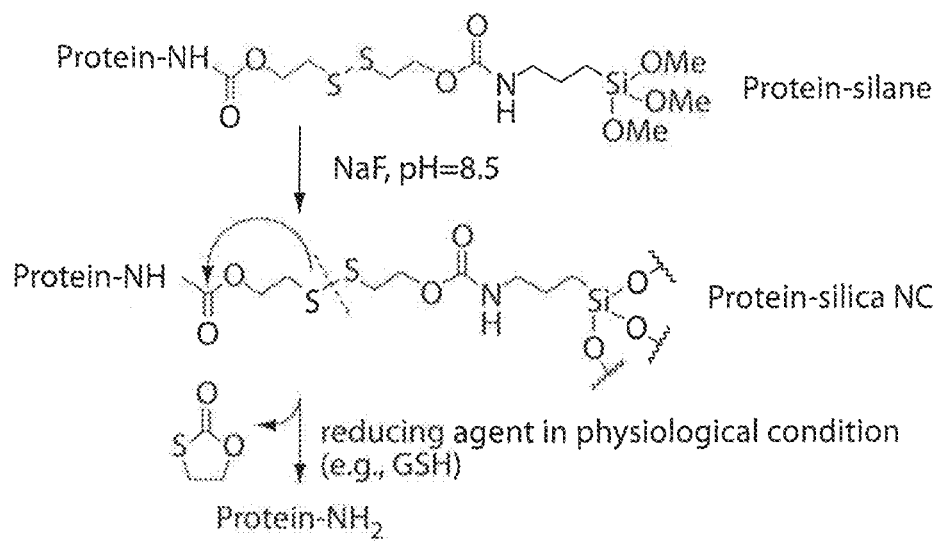
FIG. 4B
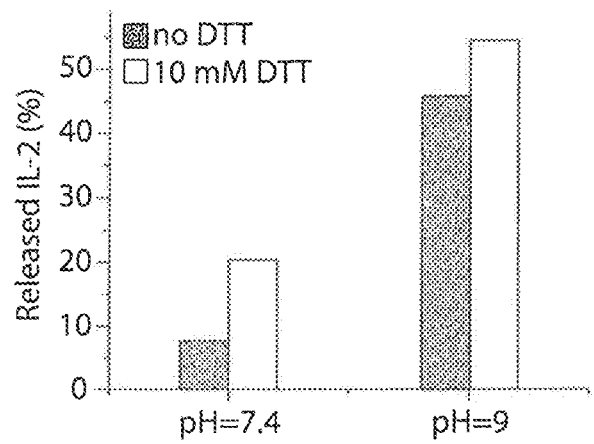
FIG. 4C

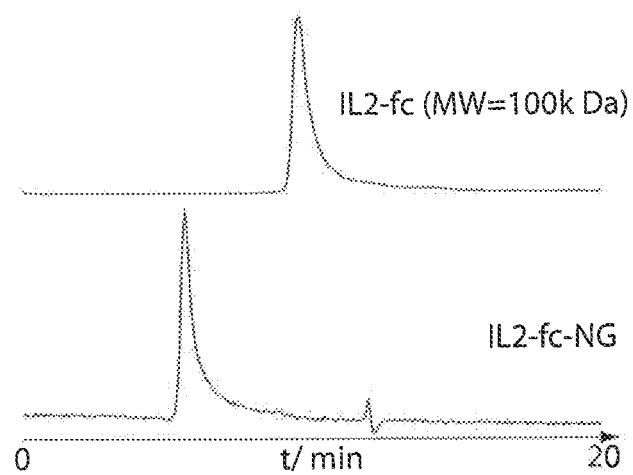
FIG. 10A
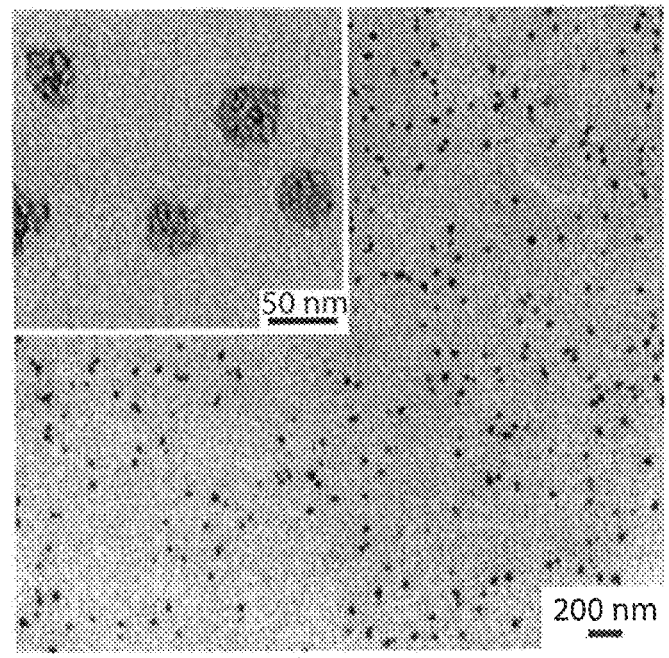
FIG. 10B
|  | Diameter (nm) | Polydispersity |
|---|---|---|
| IL2-fc-NG | 85.6±1.9 | 0.306±0.004 |
FIG. 10C

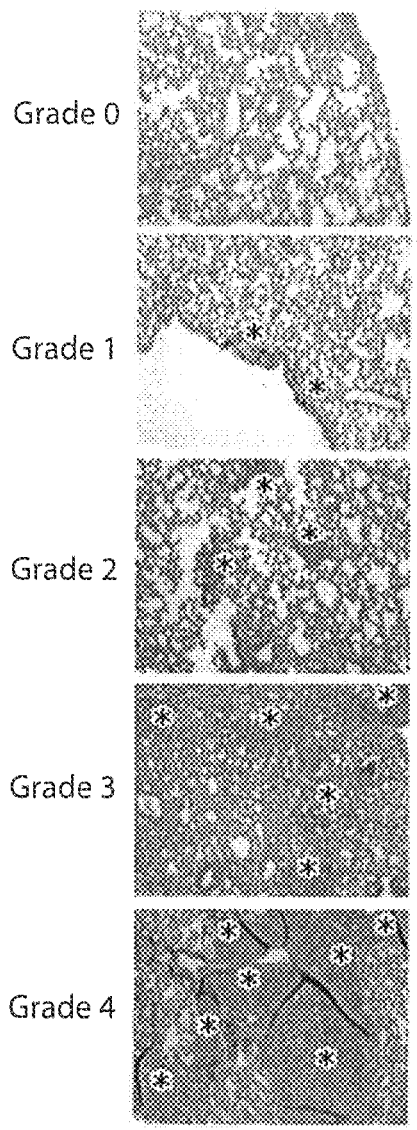
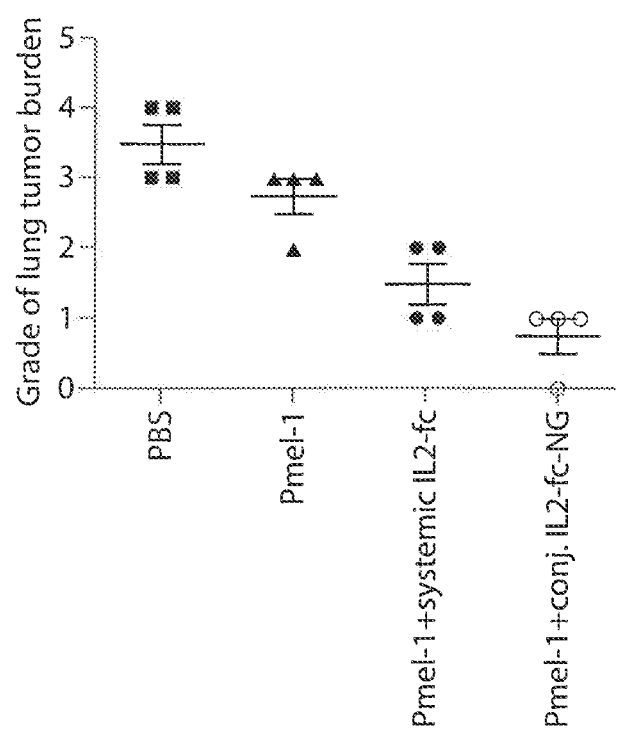
FIG. 17C
FIG. 17D

CARRIER-FREE BIOLOGICALLY-ACTIVE PROTEIN NANOSTRUCTURES

RELATED APPLICATION

This application is a continuation of U.S. patent application Ser. No. 16/451,996, filed Jun. 25, 2019, now pending, which application is a continuation of U.S. patent application Ser. No. 16/195,128, filed Nov. 19, 2018, now U.S. Pat. No. 10,357,544, which is a continuation of U.S. patent application Ser. No. 15/470,169, filed Mar. 27, 2017, now U.S. Pat. No. 10,226,510, which is a continuation of U.S. patent application Ser. No. 14/498,386, filed Sep. 26, 2014, now U.S. Pat. No. 9,603,944, which claims the benefit under 35 U.S.C. § 119(e) of U.S. provisional application No. 61/883,503, filed Sep. 27, 2013. The entire contents of each of the foregoing applications are incorporated herein in their entireties.

FIELD OF THE INVENTION

The present disclosure relates, in some embodiments, to the delivery of carrier-free, biologically-active therapeutic proteins to tissues and cells.

BACKGROUND OF THE INVENTION

Protein therapeutics, such as antibodies, cytokines, growth factors and vaccines, are important therapeutics for the treatment of a variety of diseases including, for example, cancer, diabetes and cardiovascular diseases. This class of protein therapeutics has been developed rapidly in the global pharmaceutical industry over the last few years. Protein therapeutics have the advantages of high specificity and potency relative to small molecule drugs. Nonetheless, the use of protein therapeutics is limited as a result of their intrinsic instability, immunogenicity and short half-life.

To address these limitations, there are generally two approaches: one is genetic fusion of the therapeutic protein, and the other is use of engineered carriers to deliver protein therapeutics. With engineered carriers, proteins are loaded by either encapsulation/adsorption or conjugation. Encapsulation or adsorption of proteins in/onto liposomes or nanoparticles is typically inefficient. Conjugation of proteins typically reduces their bioactivity. Thus, both approaches are problematic.

SUMMARY OF THE INVENTION

The present disclosure provides, inter alia, methods and compositions for efficient delivery of bioactive (e.g., fully bioactive) proteins. Various aspects provided herein are based, at least in part, on surprising results showing that proteins (e.g., therapeutic proteins), reversibly and covalently crosslinked to each other through a degradable linker can be delivered in vivo without a carrier (e.g., without albumin or other carrier) as bioactive proteins. Various other aspects described herein are based, at least in part, on surprising results showing that proteins, reversibly modified with functional groups and further protected from degradation by a polymer-based nanoshell, can be delivered in vivo as intact, fully bioactive proteins. Using methods provided herein, proteins can be incorporated into a delivery system with a high incorporation efficiency (e.g., greater than ~90%) and with high protein drug loading efficiency (e.g., greater than ~80%). These efficiencies are far higher than what has been achieved in the past.

Some aspects of the present disclosure provide compositions comprising a monodispersed plurality of carrier-free, biologically-active protein-polymer nanogels, wherein proteins of the nanogels are reversibly and covalently crosslinked to each other through a degradable linker, and wherein proteins of the nanogels are crosslinked to a polymer. In some embodiments, the polymer is crosslinked to the surface of a nanogel (and, thus, is considered to be surface-conjugated—see, e.g., FIG. 9A).

In some embodiments, a nanostructure (e.g., nanogel) comprises, consists of, or consists essentially of (a) one or more biologically-active proteins reversibly and covalently crosslinked to each other through a degradable linker (e.g., disulfide linker) and (b) polymers crosslinked to surface-exposed proteins of the nanogel (e.g., reversibly and covalently crosslinked through a degradable linker). In some embodiments, the weight percentage of proteins crosslinked to each other is greater than 75% w/w (e.g., greater than 80%, 85% or 90% w/w) of the nanogel.

A plurality of nanogels is considered to be "monodispersed" in a composition (e.g., an aqueous or otherwise liquid composition) if the nanogels have the same size (e.g., diameter) relative to each other. Nanogels of a plurality may be considered to have the same size relative to each other if the sizes among the nanogels in the plurality vary by no more than 5%-10%. In some embodiments, nanogels of a plurality are considered to have the same size relative to each other if the sizes among the nanogels in the plurality vary by no more than 5%, 6%, 7%, 8%, 9% or 10%. In some embodiments, nanogels of a plurality are considered to have the same size relative to each other if the sizes among the nanogels in the plurality vary by less than 5% (e.g., 4%, 3%, 2% or 1%)

Other aspects of the present disclosure provide nanogels comprising a polymer and at least 75% w/w of proteins that are reversibly and covalently crosslinked to each other through a degradable linker. In some embodiments, the degradable linker is a redox responsive linker, such as, for example, a disulfide linker (e.g., Formula I).

Yet other aspects of the present disclosure provide methods of producing a plurality of carrier-free, biologically-active protein nanogels, the methods comprising (a) contacting a protein with a degradable linker (e.g., a disulfide linker) under conditions that permit reversible covalent crosslinking of proteins to each other through the degradable linker, thereby producing a plurality of protein nanogels, and (b) contacting the protein nanogels with a polymer (e.g., polyethylene glycol) under conditions that permit crosslinking of the polymer to proteins of the protein nanogels, thereby producing a plurality of carrier-free, biologically-active protein-polymer nanogels.

In some embodiments, the conditions of (a) include contacting the protein with the degradable linker in an aqueous buffer at a temperature of 4° C. to 25° C. In some embodiments, the conditions of (a) include contacting the protein with the degradable linker in an aqueous buffer for 30 minutes to one hour. In some embodiments, the conditions of (b) include contacting the protein nanogels with the polymer in an aqueous buffer at a temperature of 4° C. to 25° C. In some embodiments, the conditions of (b) include contacting the protein nanogels with the polymer in an aqueous buffer for 30 minutes to one hour. In some embodiments, the aqueous buffer comprises phosphate buffered saline (PBS).

In some embodiments, the conditions of (a) do not include contacting the protein with the degradable linker at a temperature of greater than 30° C. In some embodiments, the conditions of (b) do not include contacting the protein nanogels with the polymer at a temperature of greater than 30° C.

In some embodiments, the conditions of (a) do not include contacting the protein with the degradable linker in an organic solvent (e.g., alcohol). In some embodiments, the conditions of (b) do not include contacting the protein nanogels with the polymer in an organic solvent.

In some embodiments, the protein is a cytokine, growth factor, antibody or antigen. For example, the protein may be a cytokine. In some embodiments, the cytokine is IL-2 or IL-2-Fc. In some embodiments, the cytokine is IL-15 or IL-15SA.

In some embodiments, the degradable linker is a redox responsive linker. In some embodiments, the redox responsive linker comprises a disulfide bond. In some embodiments, the degradable linker comprises or consists of Formula I.

In some embodiments, the polymer is a hydrophilic polymer. The hydrophilic polymer, in some embodiments, comprises polyethylene glycol (PEG). For example, the hydrophilic polymer may be a 4-arm PEG-$NH_2$ polymer.

In some embodiments, the dry size of the carrier-free, biologically-active protein-polymer nanogels is less than 100 nm in diameter. For example, the dry size of the carrier-free, biologically-active protein-polymer nanogels may be 50-60 nm in diameter. In some embodiments, protein nanogels of a plurality, as provided herein, are of similar dry size (e.g., within 1%, 2%, 3%, 4%, 5% or 10% diameter of each other).

In some embodiments, the hydrodynamic size of the carrier-free, biologically-active protein-polymer nanogels is less than 100 nm in diameter. For example, the hydrodynamic size of the carrier-free, biologically-active protein-polymer nanogels may be 80-90 nm in diameter. In some embodiments, protein nanogels of a plurality, as provided herein, are of similar hydrodynamic size (e.g., within 1%, 2%, 3%, 4%, 5% or 10%, diameter of each other).

In some embodiments, the concentration of the protein in the aqueous buffer is 10 mg/mL to 50 mg/mL (e.g., 10, 15, 20, 25, 30, 35, 40, 45 or 50 mg/mL).

In some embodiments, the plurality of carrier-free, biologically-active protein-polymer nanogels is a monodispersed plurality of carrier-free, biologically-active protein-polymer nanogels.

In some embodiments, the carrier-free, biologically-active protein-polymer nanogels do not include albumin.

In some embodiments, the weight percentage of protein (e.g., biologically-active protein, crosslinked protein) in the carrier-free, biologically-active protein-polymer nanogels is at least 75%. In some embodiments, the weight percentage of protein in the carrier-free, biologically-active protein-polymer nanogels is at least 80%. In some embodiments, the weight percentage of protein in the carrier-free, biologically-active protein-polymer nanogels is at least 85%. In some embodiments, the weight percentage of protein in the carrier-free, biologically-active protein-polymer nanogels is at least 90%.

Some aspects of the present disclosure provide methods of in vivo protein delivery, comprising administering to a subject any one of the compositions or nanogels provided herein.

In some embodiments, the subject has a disease. In some embodiments, the disease is cancer, diabetes, an autoimmune disease or a cardiovascular disease.

In some embodiments, the protein, under physiological conditions, is released in its native conformation from the nanogel and is biologically active. In some embodiments, the specific activity of the released protein is at least than 50% (e.g., at least 55%, 60%, 65%, 70%, 75%, 80%, 85%, 90%, 95%, 96%, 97%, 98%, 99% or 100%) of the specific activity of the protein before it was crosslinked to another protein through a degradable linker.

Some aspects of the disclosure provide proteins reversibly linked through a degradable linker to a polymerizable functional group. Such proteins are considered herein to be reversibly modified proteins.

In some embodiments, the polymerizable functional group comprises silane and/or a crosslinkable polymer. In some embodiments, the crosslinkable polymer comprises poly(ethylene oxide), polylactic acid and/or poly(lactic-co-glycolic acid). In some embodiments, the proteins are reversibly linked through a degradable linker to silane.

In some embodiments, proteins of the disclosure are cytokines, growth factors, antibodies or antigens. In some embodiments, the cytokine is IL-2.

In some embodiments, the degradable linker comprises an N-hydroxysuccinimide ester. In some embodiments, the degradable linker is a redox responsive linker. In some embodiments, the redox responsive linker comprises a disulfide bond.

Other aspects of the disclosure provide pluralities of any reversibly modified protein described herein.

In some embodiments, reversibly modified proteins in such pluralities are crosslinked.

Yet other aspects of the disclosure provide nanostructures that comprise a polymer and at least 50% w/w of a protein that is reversibly linked through a degradable linker to a polymerizable functional group. "w/w" here means weight of protein to weight of nanostructure (e.g., nanogel).

In some embodiments, the polymerizable functional group comprises silane and/or a crosslinkable polymer. In some embodiments, the crosslinkable polymer comprises poly(ethylene oxide), polylactic acid and/or poly(lactic-co-glycolic acid).

In some embodiments, the nanostructures comprise at least 75% w/w of a protein that is reversibly linked to a polymerizable functional group. In some embodiments, the nanostructures comprise at least 80% w/w of a protein that is reversibly linked to a polymerizable functional group. Also contemplated herein are nanostructures that comprise about 50% w/w to about 90% w/w of a protein that is reversibly linked to a polymerizable functional group. For example, in some embodiments, a nanostructure may have about 50% w/w, about 55% w/w, about 60% w/w, about 65% w/w, about 70% w/w, about 75% w/w, about 80% w/w, about 85% w/w, or about 90% w/w of a protein that is reversibly linked to a polymerizable functional group.

In some embodiments, the protein is a cytokine, growth factor, antibody or antigen. In some embodiments, the cytokine is IL-2.

In some embodiments, the nanostructures comprise a reactive group on their surface. In some embodiments, the reactive group is a maleimide, rhodamine or IR783 reactive group.

In some embodiments, the nanostructures are linked to a carrier cell. In some embodiments, the carrier cell is a nucleated carrier cell. In some embodiments, the nucleated carrier cell is a T cell, a B cell, an NK cell or an NKT cell.

In some embodiments, the nanostructures are 20-500 nm in diameter. In some embodiments, the nanostructures are 100-300 nm in diameter.

In some embodiments, the degradable linker comprises an N-hydroxysuccinimide ester. In some embodiments, the degradable linker is a redox responsive linker. In some embodiments, the redox responsive linker comprises a disulfide bond.

Still other aspects of the disclosure provide methods of producing a nanostructure, the methods comprising modifying a protein with a degradable linker and polymerizable functional groups, and polymerizing the polymerizable functional groups with a crosslinker and soluble fluoride.

In some embodiments, the polymerizable functional group comprises silane and/or a crosslinkable polymer. In some embodiments, the crosslinkable polymer comprises poly(ethylene oxide), polylactic acid and/or poly(lactic-co-glycolic acid).

In some embodiments, the soluble fluoride is sodium fluoride. In some embodiments, the soluble fluoride is potassium fluoride.

In some embodiments, the protein is a cytokine, growth factor, antibody or antigen. In some embodiments, the cytokine is IL-2.

In some embodiments, the degradable linker comprises an N-hydroxysuccinimide ester. In some embodiments, the degradable linker is a redox responsive linker. In some embodiments, the redox responsive linker comprises a disulfide bond.

In some embodiments, the nanostructure is 20-500 nm in diameter. In some embodiments, the nanostructure is 100-300 nm in diameter.

In some embodiments, the methods further comprise modifying the surface of the nanostructure with a reactive group. In some embodiments, the reactive group is a maleimide, rhodamine or IR783 reactive group.

In some embodiments, the methods further comprise linking the nanostructure to a carrier cell. In some embodiments, the carrier cell is a nucleated carrier cell. In some embodiments, the nucleated carrier cell is a T cell, a B cell, an NK cell or an NKT cell.

Further aspects of the disclosure provide methods of in vivo protein delivery, comprising administering to a subject any of the nanostructures provided herein. In some embodiments, the methods comprise administering to a subject a nanostructure that comprises a protein reversibly linked through a degradable linker to silane.

In some embodiments, the subject has a condition or disease. In some embodiments, the condition or disease is cancer, diabetes, an autoimmune disease, or a cardiovascular disease.

In some embodiments, the protein, under physiological conditions, is released in its native conformation from the nanostructure and is biologically active.

The disclosure also provides a linker that comprises or consists of Formula I:

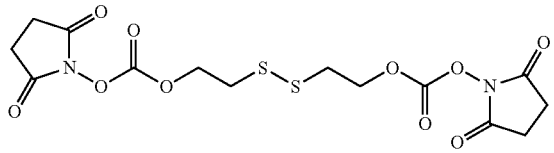 [SMILES: O=C(OCCSSCCOC(=O)ON1C(=O)CCC1=O)ON1C(=O)CCC1=O]

The disclosure further provides reversibly modified protein conjugates that comprise Formula II:

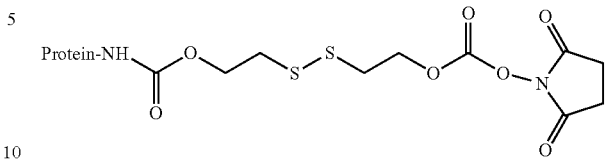

Also provided herein are reversibly modified protein conjugates that comprise Formula III:

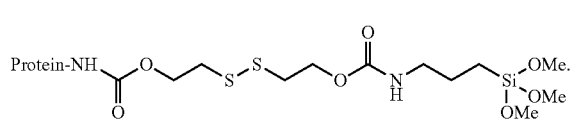

The linkers may be conjugated to the protein of interest at an amine group such as a terminal amine or an internal amine. Internal amines include side chain amines such as lysine amines.

The disclosure further provides protein conjugates comprising Formula III:

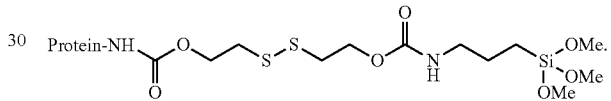

wherein the protein is a cytokine such as, for example, IL-2. Unexpectedly, silica-based nanostructures with a high incorporation efficiency (e.g., >~90%) and with high protein drug loading efficiency (e.g., >~80%) are formed by the polymerization of proteins that are reversibly modified with silane. Thus, provided herein are nanostructures formed by the polymerization of protein conjugates of Formula III with crosslinkers such as, for example, silane-PEG-silane polymers.

BRIEF DESCRIPTION OF DRAWINGS

FIG. 4A shows incorporation efficiency and loading efficiency of IL2-fc in IL2-fc-silica NCs. Incorporation efficiency[a]=conjugated IL2-fc in IL2-fc-NC/total IL2-fc added in reaction; Loading[b]=mass of conjugated IL2-fc/total mass of IL2-fc-NC. FIG. 4B shows that protein-silica NC can release the incorporated protein in its original form under physiological conditions. FIG. 4C shows release kinetics of IL-2-fc from IL-2-fc-NC incubated in buffer of different pH at 37° C. for 48 h.

FIG. 8A shows a 4 arm-PEG-NH2 that was reacted with Linker-1 to form the 4 arm-PEG-Linker-1, which bears NHS ester at the end of PEG polymer chain. FIG. 8B shows a 4 arm-PEG-Linker-1 crosslinked by protein (e.g., IL-2), which has multiple amine groups forming IL-2-PEG nanogel.

FIGS. 10A-10C show an analysis of a covalently cross-linked protein nanogel with HPLC equipped with a size exclusion column (FIG. 10A); transmission electron microscopy (FIG. 10B); and dynamic light scattering (FIG. 10C) characterizations of the nanogels for size and morphology.

FIG. 15A shows a time course of mice with established lung metastases of B 16F10 melanoma that were lympho-depleted and that received adoptive transfer of luciferase-expressing Pmel-1 melanoma-specific CD8+ T-cells with no further treatment, free IL2-Fc or surface-conjugated IL2-Fc nanogel respectively in each group. FIG. 15B shows bioluminescence images of T-cell expansion over time. FIG. 15C shows a graph quantifying bioluminescence signal in the whole body of the mice.

FIGS. 17A-17D shows inhibition of metastatic tumors in lungs. FIG. 17A shows representative images of harvested lungs from each group. FIG. 17B shows a graph of the number of tumor nodules (counted manually) in lungs. FIG. 17C shows histological images of lung tissue sections that were graded for the severity of lung metastases. FIG. 17D shows a graph of the average grade of each group.

DETAILED DESCRIPTION OF THE INVENTION

Figure 1:
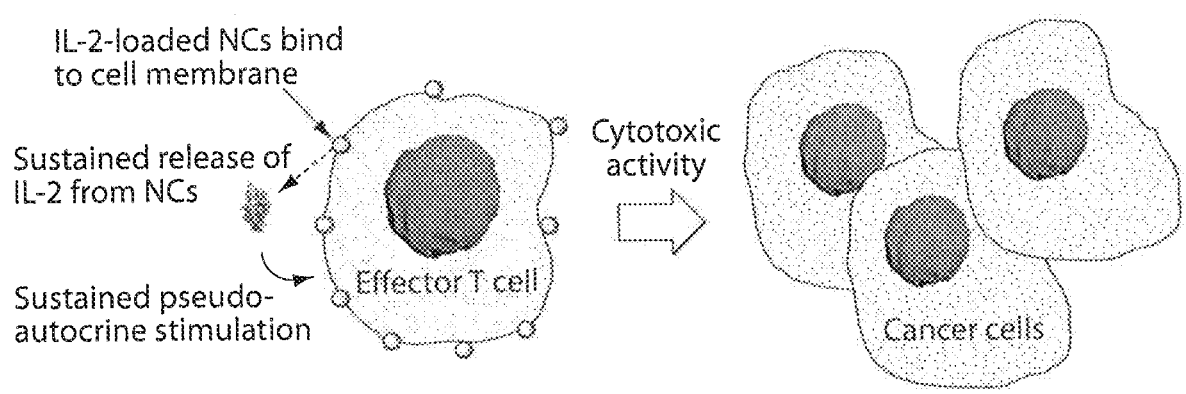
FIG. 1 shows a schematic of a T lymphocyte engineering with surface-conjugated interleukin-2 (IL-2)-loaded nanocapsules (NCs) for targeted cancer therapy.

Cancer immunotherapy, including adoptive T cell therapy, is a promising strategy to treat cancer because it harnesses a subject's own immune system to attack cancer cells. Nonetheless, a major limitation of this approach is the rapid decline in viability and function of the transplanted T lymphocytes. In order to maintain high numbers of viable tumor-specific cytotoxic T lymphocytes in tumors, co-administration of immunostimulatory agents with transferred cells is necessary. When given systemically at high doses, these agents could enhance the in vivo viability of transferred (i.e., donor) cells, improve the therapeutic function of transferred cells, and thus lead to overall improved efficacy against cancer; however, high doses of such agents could also result in life-threatening side effects. For example, the use of interleukin-2 (IL-2) as an adjuvant greatly supports adoptive T cell therapy of melanoma, where IL-2 provides key adjuvant signals to transferred T cells but also elicits severe dose-limiting inflammatory toxicity and expands regulatory T cells (Tregs). One approach to focus adjuvant activity on the transferred cells is to genetically engineer the transferred cells to secrete their own supporting factors. The technical difficulty and challenges as well as the high cost for large-scale production of genetically engineered T lymphocytes have significantly limited the potential of this method in clinical applications, to date.

Provided herein, in some aspects, is a technology platform that permits simple, safe and efficient delivery of biologically-active proteins (e.g., adjuvants such as IL-2) to therapeutic cells through chemical conjugation of protein-loaded, carrier-free nanostructures or protein-loaded silica-based nanostructures directly onto the plasma membrane of transferred cells, enabling continuous pseudoautocrine stimulation of transferred cells in vivo. In some embodiments, proteins of the disclosure are reversibly and covalently crosslinked to each other through a degradable linker to form a nanostructure such that the intact, biologically-active proteins are released from the nanostructure under physiological conditions, and optionally in the presence of a reducing agent (e.g., glutathione). In other embodiments, proteins of the disclosure are reversibly modified and "ensheathed" into silica-based nanostructures such that the intact, biologically-active proteins are released from the nanostructure under physiological conditions, and optionally in the presence of a reducing agent (e.g., glutathione). Surprisingly, nanostructures (e.g., carrier-free nanogels and/or silica-based nanostructures) of the disclosure prevent protease degradation of the loaded protein and permit its sustained local release, thereby promoting the expansion of cytotoxic T cells and avoiding systemic toxicity associated with high-doses of some proteins (e.g., IL-2, IL-15). Unexpectedly, T cells with an optimal number of nanostructures conjugated per cell maintain their cellular functions and cancer targeting and killing capability. Thus, the compositions and methods of the disclosure can, in some embodiments, augment T cell expansion and minimize systemic side effects of adjuvant drugs in vivo.

In addition to the foregoing, the present disclosure further contemplates other nanostructures that comprise other protein therapeutics for purposes other than adjuvant effect on adoptively-transferred cells. Those of skill in the art will readily recognize that the disclosure has broader applications, as provided herein.

In some embodiments, proteins of protein nanostructures of the present disclosure are reversibly linked to each other through a degradable linker (e.g., a disulfide linker) such that under physiological conditions, the linker degrades and releases the intact, biologically-active protein. In other embodiments, proteins of nanostructures are reversibly linked to functional groups through a degradable linker such that under physiological conditions, the linker degrades and releases the intact, biologically-active protein. In each instance, the proteins are considered to be reversibly modified, as described below.

A protein that is "reversibly linked to another protein" herein refers to a protein that is attached (e.g., covalently attached) to another protein through a degradable linker. Such proteins are considered to be linked (e.g., crosslinked) to each other through the degradable linker. In some embodiments, nanostructures (e.g., nanogels) contain a single (e.g., single type of) biologically-active protein (e.g., IL-2, or IL-2-Fc), while in other embodiments, nanostructures contain more than one (e.g., 2, 3, 4, 5 or more) of biologically-active protein (e.g., a combination of different proteins such as IL-2 and IL-15 (or IL-15SA)). For example, a protein nanogel may contain a combination of Protein A and Protein B, wherein Protein A is linked to Protein A, Protein A is linked to Protein B and/or Protein B is linked to Protein B.

A protein that is "reversibly linked to a functional group," or a protein that is "reversibly modified," herein refers to a protein that is attached (e.g., covalently attached) to a functional group through a degradable linker. Such a protein may be referred to herein as a "protein conjugate" or a "reversibly modified protein conjugate"—the terms may be used interchangeably herein. It should be understood that proteins and polymers each contain functional groups to which a protein can be linked via a reversible linker (e.g., degradable linker such as a disulfide linker). Examples of protein conjugates and reversibly modified proteins, as provided herein, include without limitation, a protein reversibly linked (e.g., via a degradable linker) to another protein, a protein reversibly linked to a polymer, and a protein reversibly linked to another functional group. It should be understood that the term "protein" includes fusion proteins.

The degradable linkers provided herein, in some embodiments, comprise an N-hydroxysuccinimide ester, which is capable of reacting with proteins at neutral pH (e.g., about 6 to about 8, or about 7) without denaturing the protein. In some embodiments, the degradable linkers are "redox responsive" linkers, meaning that they degrade in the presence of a reducing agent (e.g., glutathione, GSH) under physiological conditions (e.g., 20-40° C. and/or pH 6-8), thereby releasing intact protein from the compound to which it is reversibly linked. An example of a degradable linker for use in accordance with the present disclosure is the following:

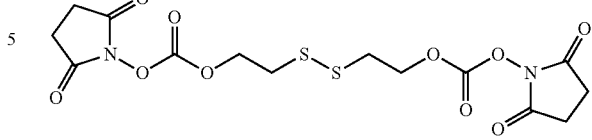

Formula I

The linker of Formula I contains a disulfide, which is cleaved in the presence of a reducing agent. For example, under physiological conditions, the disulfide bond of the linker of Formula I is cleaved by glutathione.

Proteins may be linked (e.g., covalently linked) to a degradable linker through any terminal or internal —NH$_2$ functional group (e.g., side chain of a lysine). Thus, an intermediate species formed during the reversible modification of a protein with a degradable linker of Formula I is the following:

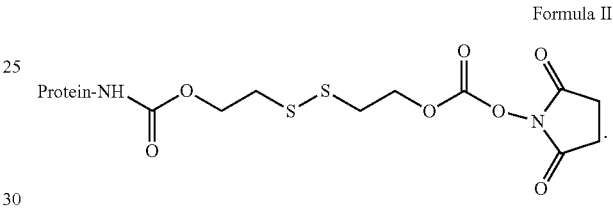

Formula II

Figure 7:
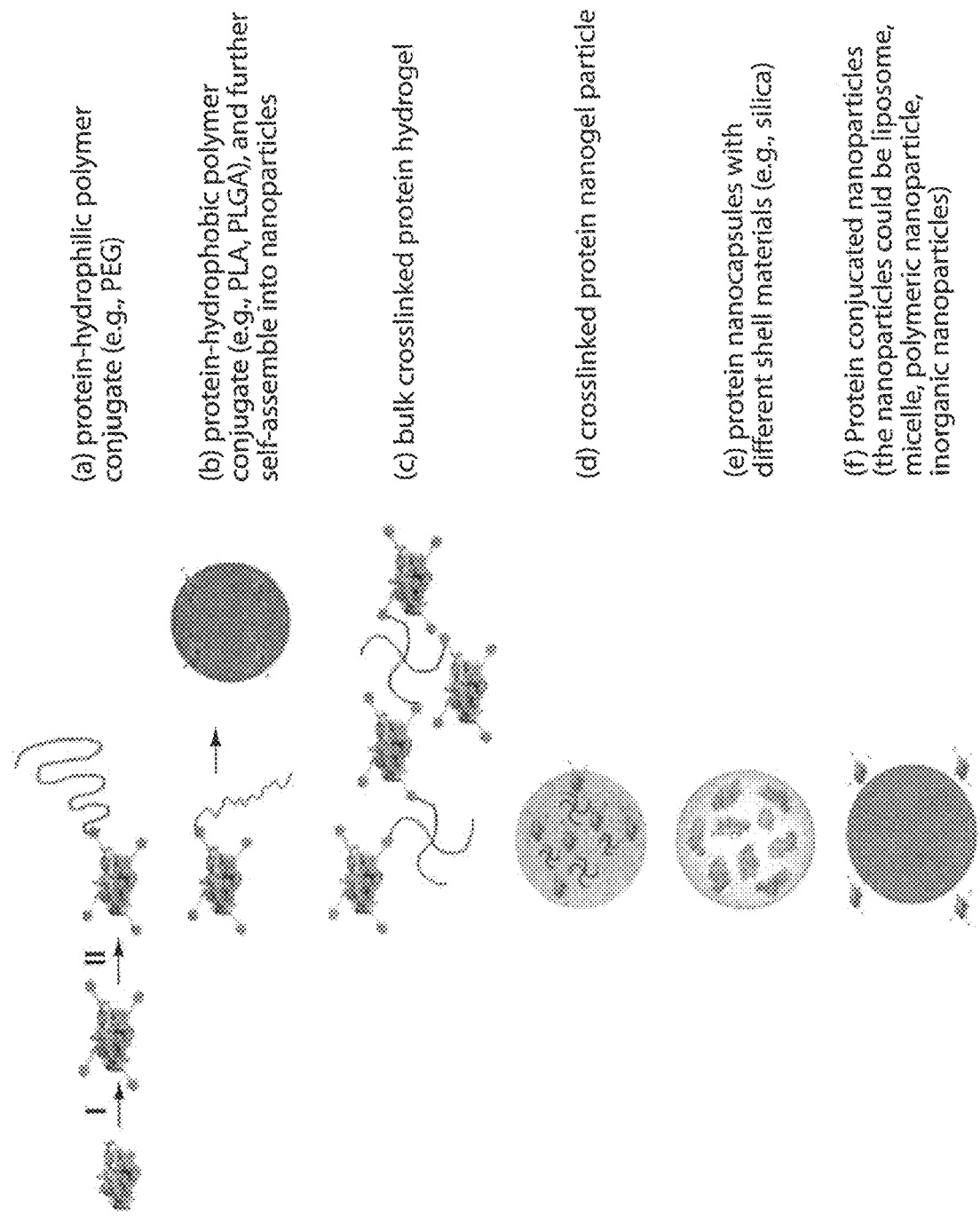
FIG. 7 shows a schematic of various structures constructed with reversibly modified proteins.

Reversibly modified proteins provided herein can, in some embodiments, be formed or self-assemble into various nanostructures including, without limitation, protein-hydrophilic polymer conjugates (e.g., reversibly modified with PEG; FIG. 7A), protein-hydrophobic polymer conjugates (e.g., reversibly modified PLA or PLGA; FIG. 7B), bulk crosslinked protein hydrogels (FIG. 7C), crosslinked protein nanogel particles (FIG. 7D), protein nanocapsules with different shell materials (e.g., silica; FIG. 7E), protein-conjugated nanoparticles (e.g., liposome, micelle, polymeric nanoparticles, inorganic nanoparticles; FIG. 7F). Likewise, proteins crosslinked to each other, as provided herein, in some embodiments, can be formed or can self-assemble into protein nanostructures (e.g., FIG. 9A).

In some embodiments, protein nanostructures (e.g., protein nanogels, including protein-polymer nanogels) of the present disclosure do not contain carrier proteins or other carrier molecules. For example, in some embodiments, protein nanostructures do not contain albumin (e.g., bovine serum albumin (BSA)). Carrier proteins typically facilitate the diffusion and/or transport of different molecules. It should be understood that the term "carrier protein," as used herein, refers to a protein that does not adversely affect a biologically-active protein of a protein nanostructure. In some embodiments, a carrier protein is an inert protein. Thus, in some embodiments, carrier proteins are not biologically active. Nanostructures of the present disclosure, in some embodiments, do not require carrier proteins or other carrier molecules to facilitate their transport to and into cells and tissue in vivo.

It should be understood that nanogels of the present disclosure, in some embodiments, contain one or more (e.g., 2, 3, 4, 5 or more) therapeutic proteins (e.g., IL-2 and/or IL-15 (or IL15-SA)) crosslinked to each other through a degradable linker (e.g., disulfide linker). Such nanogels no not contain an inert carrier protein, such as albumin.

Examples of proteins for use in accordance with the present disclosure include, without limitation, antibodies, single chain antibodies, antibody fragments, enzymes, co-factors, receptors, ligands, transcription factors and other regulatory factors, some antigens (as discussed below), cytokines, chemokines, and the like. These proteins may or may not be naturally occurring. Other proteins are contemplated and may be used in accordance with the disclosure. Any of the proteins can be reversibly modified through a redox responsive (e.g., disulfide) with a silane group to, for example, form a silica-based nano structure.

In some embodiments, proteins of the disclosure are immunostimulatory proteins. As used herein, an immunostimulatory protein is a protein that stimulates an immune response (including enhancing a pre-existing immune response) in a subject to whom it is administered, whether alone or in combination with another protein or agent. Examples of immunostimulatory proteins that may be used in accordance with the disclosure include, without limitation, antigens, adjuvants (e.g., flagellin, muramyl dipeptide), cytokines including interleukins (e.g., IL-2, IL-7, IL-15 (or superagonist/mutant forms of these cytokines, such as, for example, IL-15SA), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunostimulatory proteins are contemplated and may be used in accordance with the disclosure.

In some embodiments, proteins of the disclosure are antigens. Examples of antigens that may be used in accordance with the disclosure include, without limitation, cancer antigens, self-antigens, microbial antigens, allergens and environmental antigens. Other protein antigens are contemplated and may be used in accordance with the disclosure.

In some embodiments, proteins of the disclosure are cancer antigens. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)—0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-C5. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2. Other cancer antigens are contemplated and may be used in accordance with the disclosure.

In some embodiments, proteins of the disclosure are antibodies or antibody fragments including, without limitation, bevacizumab (AVASTIN®), trastuzumab (HERCEPTIN®), alemtuzumab (CAMPATH®, indicated for B cell chronic lymphocytic leukemia,), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-C5, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure.

Proteins of the disclosure may be modified in a binary solvent that is compatible with proteins. For example, in some embodiments, a binary solvent includes aqueous buffer and a water-miscible organic solvent, such as phosphate buffered saline (PBS) and dimethyl sulfoxide (DMSO), and is used for reversibly modifying a protein with a degradable linker. The ratio of the aqueous buffer (e.g., PBS) to organic phase (e.g., DMSO) may be within a range of about 50:1 to about 20:1. In some embodiments, the ratio of inorganic phase to organic phase is about 30:1 to about 20:1, or about 25:1 (e.g., 500 µL:20 µL). In some embodiments, the organic solvent is less than 5% of the total volume of the binary buffer or the reaction containing the binary buffer.

A "polymerizable functional group," as used herein, refers to a group of atoms and bonds that can chemically react to form a polymer chain or network. A "polymer" refers to a chain or network of repeating units or a mixture of different repeating units. As used herein, a polymer is itself a functional group. Examples of polymerizable functional groups for use in accordance with the disclosure include, without limitation, silane, ethylene oxide, lactic acid, lactide, glycolic acid, N-(2-hydroxypropyl)methacrylamide, silica, poly(ethylene oxide), polylactic acid, poly(lactic-co-glycolic acid), polyglutamate, polylysine, cyclodextrin and dextran chitosan. Other polymerizable functional groups are contemplated and may be used in accordance with the disclosure. It should be understood, however, that a "polymer," as used herein, is not a protein (is a non-protein), peptide (is a non-peptide) or amino acid (is a non-amino acid).

It should be understood that the term "polymer" encompasses "co-polymer." That is, a polymer may comprise a mixture of different functional groups (e.g., silane-PEG-silane), including shorter polymers or co-polymers. The functional groups are typically polymerized under protein-compatible, neutral conditions. Thus, in some embodiments, polymerization of the functional groups occurs in an at least partially aqueous solution at about pH 6 to about pH 8. For example, polymerization of the functional groups can occur at pH 6, pH 6.5, pH 7, pH 7.5 or pH 8. In some embodiments, polymerization of the functional groups occurs at about pH 7.

In some embodiments, the polymerization reaction is catalyzed by sodium fluoride, potassium fluoride or any other soluble fluoride.

Exemplary polymers that can be reversibly linked to proteins and/or used to form nanostructures (e.g., nanocapsules, nanogels, hydrogels) include, without limitation, aliphatic polyesters, poly (lactic acid) (PLA), poly (glycolic acid) (PGA), co-polymers of lactic acid and glycolic acid (PLGA), polycarprolactone (PCL), polyanhydrides, poly (ortho)esters, polyurethanes, poly(butyric acid), poly(valeric acid), and poly(lactide-co-caprolactone), and natural polymers such as alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Other polymers are contemplated and may be used in accordance with the disclosure.

Figure 9A:
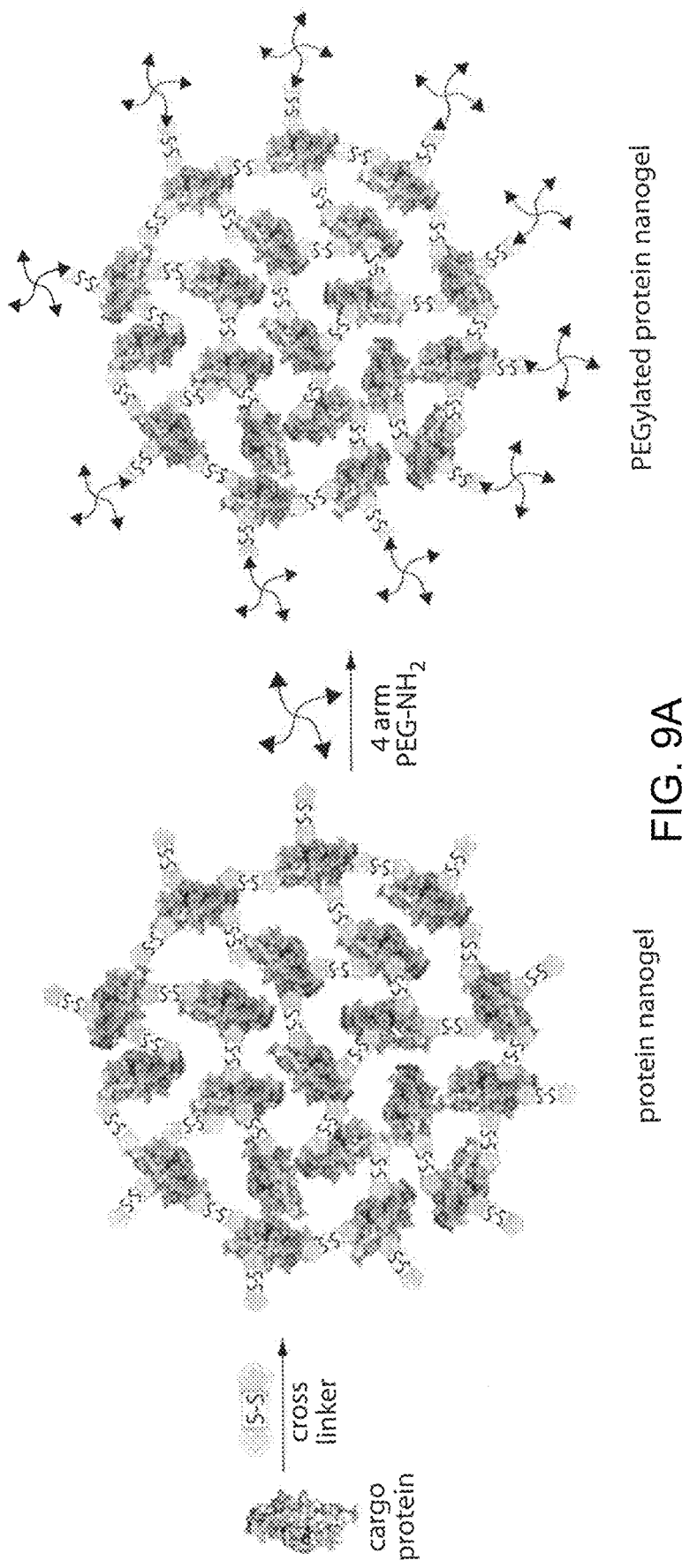
FIG. 9A shows a schematic of one example of a method for preparing a covalently crosslinked protein nanogel.
Figure 9B:
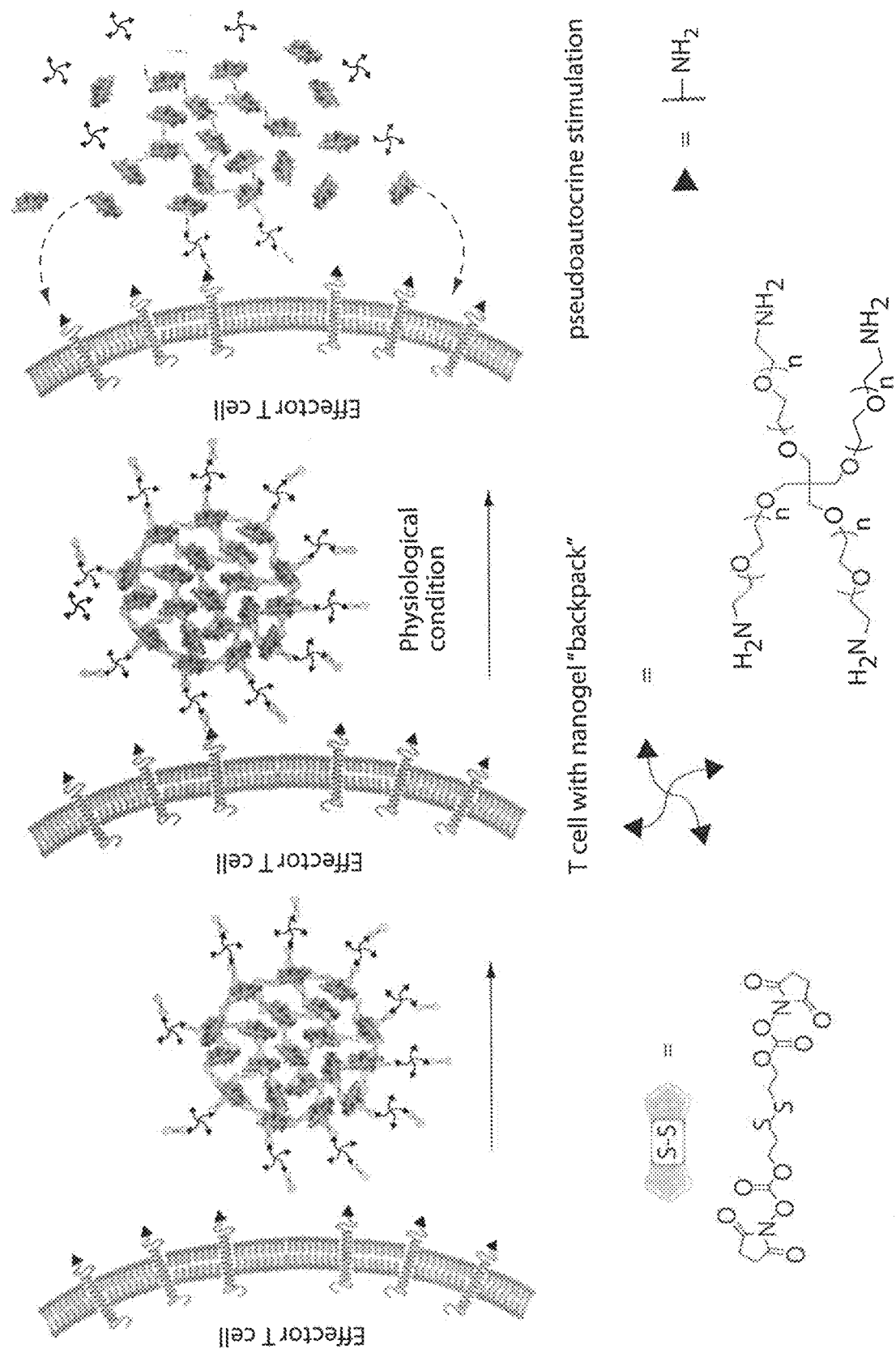
FIG. 9B shows a schematic of one example of a method for conjugating a protein nanogel to a cell surface and the release of intact, biologically-active protein.

In some aspects of the disclosure, proteins are reversibly linked to hydrophilic polymers such as, for example, polyethylene glycol (PEG) (FIG. 7A and FIGS. 9A-9B).

In other aspects of the disclosure, proteins are reversibly linked to hydrophobic polymers such as, for example, polylactic acid (PLA) and/or poly(lactic-co-glycolic acid) (PLGA). These protein-hydrophobic polymer conjugates can, in some embodiments, self-assemble into nanoparticles (FIGS. 7B and 7F).

The protein conjugates of the present disclosure, in some embodiments, may be crosslinked to form a hydrogel network (FIG. 7C), nanogel particle (FIG. 7D), or protein nanogel (FIG. 9A), all of which are herein considered to be "nanostructures."

A protein "nanostructure," as used herein, refers to a plurality of crosslinked protein conjugates (e.g., protein reversibly linked through a degradable linker to a functional group or polymer, or "reversibly modified") wrapped in a polymer-based, or silica, nanoshell (FIG. 7E). The nanoshell is formed, in some embodiments, by polymerizing functional groups (e.g., silanes) of a protein conjugate with a crosslinker (e.g., silane-PEG-silane) in the presence of a catalyst (e.g., NaF). An example of a protein nanostructure is a "protein nanogel," which refers to a plurality of proteins crosslinked (e.g., reversibly and covalently crosslinked) to each other through a degradable linker (see, e.g., FIG. 9A). In some embodiments, proteins of a nanogel are crosslinked (e.g., reversibly and covalently crosslinked) to a polymer (e.g., a hydrophilic polymer such as polyethylene glycol (PEG); see, e.g., FIG. 9A). The polymer, in some embodiments, may be crosslinked to the surface of the nanogel (e.g., to proteins exposed at the surface of the nanogel).

The size of a protein nanogel may be determined at least two ways: based on its "dry size" and based on its "hydrodynamic size." The "dry size" of a protein nanogel refers to the diameter of the nanogel as a dry solid. The "hydrodynamic size" of a protein nanogel refers to the diameter of the nanogel as a hydrated gel (e.g., a nanogel in an aqueous buffer). The dry size of a nanogel may be determined, for example, by transmission electron microscopy, while the hydrodynamic size of the nanogel may be determined, for example, by dynamic light scattering.

In some embodiments, the dry size of a nanogel is less than 100 nm. In some embodiments, the dry size of a nanogel is less than 95 nm, less than 90 nm, less than 85 nm, less than 80 nm, less than 75 nm, less than 70 nm, less than 65 nm, or less than 60 nm. In some embodiments, the dry size of a nanogel is 40 to 90 nm, 40 to 80 nm, 40 to 70 nm, 40 to 60 nm, 50 to 90 nm, 60 to 80 nm, 50 to 70 nm, or 50 to 60 nm. In some embodiments, the dry size of a nanogel is 40 nm, 45 nm, 50 nm, 55 nm, 60 nm, 65 nm, 70 nm, 75 nm, 80 nm, 85 nm, 90 nm or 95 nm.

In some embodiments, the average dry size of a nanostructure (e.g., nanogel) within a plurality of nanostructures is less than 100 nm. In some embodiments, the average dry size of a nanostructure within such a plurality varies by no more than 5% or 10%. In some embodiments, the average dry size of a nanostructure (e.g., nanogel) within a plurality of nanostructures is less than 95 nm, less than 90 nm, less than 85 nm, less than 80 nm, less than 75 nm, less than 70 nm, less than 65 nm, or less than 60 nm. In some embodiments, the average dry size of a nanostructure (e.g., nanogel) within a plurality of nanostructures is 40 to 90 nm, 40 to 80 nm, 40 to 70 nm, 40 to 60 nm, 50 to 90 nm, 60 to 80 nm, 50 to 70 nm, or 50 to 60 nm. In some embodiments, the dry size of a nanogel is 40 nm, 45 nm, 50 nm, 55 nm, 60 nm, 65 nm, 70 nm, 75 nm, 80 nm, 85 nm, 90 nm or 95 nm.

In some embodiments, the hydrodynamic size of a nanogel is less than 100 nm. In some embodiments, the dry size of a nanogel is less than 95 nm, less than 90 nm, less than 80 nm, less than 85 nm, or less than 75 nm. In some embodiments, the hydrodynamic size of a nanogel is 70 to 90 nm, 70 to 85 nm, 70 to 80 nm, 75 to 90 nm, 75 to 85 nm, 75 to 80 nm, 80 to 90 nm, 80 to 85 nm or 85 to 90 nm. In some embodiments, the hydrodynamic size of a nanogel is 70 nm, 75 nm, 80 nm, 85 nm, 90 nm, or 95 nm. In some embodiments, the hydrodynamic size of a nanogel is 80 nm, 81 nm, 82 nm, 83 nm, 84 nm, 85 nm, 86 nm, 87 nm, 88 nm, 89 nm or 90 nm.

In some embodiments, the average hydrodynamic size of a nanostructure (e.g., nanogel) within a plurality of nanostructures is less than 100 nm. In some embodiments, the average hydrodynamic size of a nanostructure within such a plurality varies by no more than 5% or 10%. In some embodiments, the average hydrodynamic size of a nanostructure (e.g., nanogel) within a plurality of nanostructures is less than 95 nm, less than 90 nm, less than 80 nm, less than 85 nm, or less than 75 nm. In some embodiments, the average hydrodynamic size of a nanostructure (e.g., nanogel) within a plurality of nanostructures is 70 to 90 nm, 70 to 85 nm, 70 to 80 nm, 75 to 90 nm, 75 to 85 nm, 75 to 80 nm, 80 to 90 nm, 80 to 85 nm or 85 to 90 nm. In some embodiments, the average hydrodynamic size of a nanostructure (e.g., nanogel) within a plurality of nanostructures is 70 nm, 75 nm, 80 nm, 85 nm, 90 nm, or 95 nm. In some embodiments, the average hydrodynamic size of a nanostructure (e.g., nanogel) within a plurality of nanostructures is 80 nm, 81 nm, 82 nm, 83 nm, 84 nm, 85 nm, 86 nm, 87 nm, 88 nm, 89 nm or 90 nm.

In some embodiments, nanostructures are provided in a dry, solid form, such as a lyophilized form. In other embodiments, nanostructures are provided in a hydrated form, such as in aqueous or otherwise liquid solution.

Nanostructures, in some embodiments, are substantially spherical nanocapsules or nanoparticles. In some embodiments, the diameter of a nanostructure ranges from 1-1000 nanometers (nm). In some embodiments, the diameter ranges in size from 20-750 nm, or from 20-500 nm, or from 20-250 nm. In some embodiments, the diameter ranges in size from 50-750 nm, or from 50-500 nm, or from 50-250 nm, or from about 100-300 nm. In some embodiments, the diameter is about 100, about 150, about 200, about 250 nm, or about 300 nm.

As discussed herein, the nanostructures may be modified or synthesized to comprise one or more reactive groups on their exterior surface for reaction with reactive groups on cell carriers (e.g., T cells). These nanostructure reactive groups include, without limitation, thiol-reactive maleimide head groups, haloacetyl (e.g., iodoacetyl) groups, imidoester groups, N-hydroxysuccinimide esters, pyridyl disulfide groups, and the like. These reactive groups react with groups on the carrier cell surface and, thus, the nanostructures are bound to the cell surface. It will be understood that when surface modified in this manner, the nanostructures are intended for use with specific carrier cells having "complementary" reactive groups (i.e., reactive groups that react with those of the nanostructures). In some embodiments, the nanostructures will not integrate into the lipid bilayer that comprises the cell surface. Typically, the nanostructures will not be phagocytosed (or internalized) by the carrier cells.

In some embodiments the nanostructures do not comprise antibodies or antibody fragments on their surface, while in other embodiments they do. In some embodiments the nanostructures do not comprise antibodies or antibody fragments that are specific to T cell surface moieties (or exogenous moieties coated onto a T cell surface such other antibodies or antibody fragments), while in other embodiments they do. Thus, in some embodiments the nanostructures themselves do not stimulate carrier cell activation simply by binding to the carrier cell. In other embodiments, however, the nanostructures do stimulate carrier cell activation by binding to the carrier cell (e.g., binding of the nanostructures results in crosslinking of cell surface moieties and this activates the carrier cell).

The nanostructures may be covalently conjugated (or attached or bound, as the terms are used interchangeably herein), or they may be non-covalently conjugated to the carrier cells. Covalent conjugation typically provides a more stable (and thus longer) association between the nanostructures and the carrier cells. Covalent conjugation, in some embodiments, also can provide stability and thus more sustained localized delivery of agents in vivo. Non-covalent conjugation includes, without limitation, absorption onto the cell surface and/or lipid bilayer of the cell membrane.

In some instances, covalent attachment can be achieved in a two-step process in which carrier cells are first incubated with maleimide-bearing nanostructures to allow conjugation to the cell surface, followed by in situ PEGylation with thiol-terminated poly(ethylene glycol) (PEG) to cap remaining maleimide groups of the particles and avoid particle-mediated crosslinking of cells.

Carrier Cells

The carrier cells are the cells to which the nanostructures are conjugated and which, when administered in vivo, preferably home to target site(s). Suitable target cells are chosen based on their homing potential, their cell surface phenotype (for conjugation to the nanoparticles), and their ability to carry but not significantly endocytose the nanostructures. In some embodiments described herein, T cells are suitable carrier cells. The T cells may be CD4+ or CD8+ T cells. Other suitable cells include B cells, NK cells, NK T cells, and hematopoietic progenitor cells including, without limitation, murine lineage-negative, Sca-1-positive and c-kit-positive cells and their human counterparts. Substantial levels of free thiol (—SH) groups exist on the surfaces of T cells, B cells and hematopoietic progenitor cells (data not shown), thereby facilitating conjugation of nanocapsules to such cells.

Carrier cells, in some embodiments, can extravasate from blood vessels (particularly when administered by intravenous injection) and thereby enter target tissues or organs. Red blood cells typically are not able to exit the blood stream. Accordingly, one important class of carrier cells includes nucleated carrier cells. Thus, in some embodiments, carrier cells are not red blood cells. In other embodiments, carrier cells are red blood cells.

Some embodiments of the present disclosure refer to isolated carrier cells. Isolated carrier cells are cells that have been separated from the environment in which they naturally occur (i.e., they are not present in vivo). T cells in vitro are an example of an isolated cell. It should be understood that carrier cells may be isolated from their in vivo environment, conjugated to nanostructures of the present disclosure, and then re-introduced in vivo. Such carrier cells are still considered to be isolated cells.

The carrier cells, in some embodiments, are autologous to a subject being treated. In other embodiments, the carrier cells are non-autologous (yet preferably MHC matched cells).

The carrier cells typically have a half-life in vivo, following administration (or re-infusion, in some instances) of at least 48 hours, at least 3 days, at least 4 days, at least 5 days, at least 6 days, at least 7 days, or more.

The carrier cells, in some embodiments, are genetically engineered to express one or more factors including, without limitation, co-stimulatory molecules or receptors including chimeric receptors. In other embodiments, the carrier cells are not genetically engineered. In some embodiments, the carrier cells are isolated and naturally occurring (i.e., they have not been genetically or otherwise engineered).

Depending on their nature and function, the carrier cells, in some embodiments, are manipulated prior to conjugation with the nanostructures. The carrier cells, however, need not be surface-modified in order to facilitate conjugation of the nanostructures. In some of embodiments, instead, reactive groups that normally exist on the carrier cell surface are used without having to incorporate reactive groups or other entities onto the cell surface. As a result, such carrier cells do not require the presence of exogenous entities such as antibodies or antibody fragments, among others, on their surface in order to conjugate to nanostructures.

Such manipulation may also involve activation of the carrier cells, as is routinely performed for T cells. The carrier cells may, in some embodiments, be expanded and/or activated (or stimulated, as the terms are used interchangeably herein) in vitro prior to mixing with nanostructures. Expansion and activation protocols will vary depending on the carrier cell type but can include incubation with one or more cytokines, incubation with one or more cell types, and incubation with one or more antigens. If the carrier cell is a T cell, then activation may be performed by incubating the T cells with IL-2, IL-15, IL-15 superagonist, costimulatory molecules such as B7, B7.2, CD40, antibodies to various T cell surface molecules including antibodies to cell surface receptors, anti-CD3 antibodies, anti-CD28 antibodies, anti-CTLA-4 antibodies, anti-CD4OL antibodies, and the like. In some embodiments, the carrier cells and more particularly the T cells, are not coated with exogenous antibodies on their cell surface (i.e., the cells have not been contacted with antibodies or antibody fragments in vitro prior to administration).

Expansion may be measured by proliferation assays involving incorporation of radiolabeled nucleotides such as tritiated thymidine. Activation may be measured by production of cytokines such as IL-2, gamma-IFN, IL-1, IL-4, IL-6 and TNF, among others. Other ways of measuring expansion and activation are known in the art and may be used in accordance with the disclosure.

Carrier cells may be selected prior to administration to a subject in order to enrich and thus administer higher numbers of such cells in smaller volumes and/or to remove other, potentially unwanted, cells from the administered composition. Selection may involve positive or negative selection including, for example, column or plate based enrichment protocols that are known in the art.

T and B cells may be harvested from the peripheral blood of a subject.

Hematopoietic progenitor cells may be obtained from a number of sources including but not limited to cord blood, bone marrow, mobilized peripheral blood and, in some instances, differentiated embryonic stem cells.

Hematopoietic progenitor cells have been characterized in the art. Such cells in the human generally have minimally a CD34+ phenotype, although they may also be CD59+, Thy1/CD90+, CD38$^{lo/neg}$, CD33−, and/or c-kit/CD117+. They also are characterized as not expressing lineage specific markers. They can be harvested from bone marrow, cord blood or peripheral blood using affinity columns, magnetic beads, fluorescence activated cell sorting (FACS), some combination thereof, and the like. These cells have the ability to repopulate one or more hematopoietic lineages upon transplantation. Preferably, these cells repopulate more than one lineage, and even more preferably, all lineages. Repopulation or population of lineages as used herein refers to the differentiation of the stem cell into one or more lineages such that progeny of the stem cell contribute to the make-up of that lineage in the subject. It does not, however, require that the entire lineage compartment derive from the transplanted cells, however in some instances this may occur.

Isolated stem cells may be obtained by fractionating a heterogeneous cell population according to one or more markers, including by not limited to cell surface markers.

The carrier cells may be eukaryotic cells, such as mammalian cells (e.g., human cells). Alternatively, they may be non-mammalian cells. In still other embodiments, the carrier cells may be prokaryotic cells (e.g., bacterial cells). Several bacterial cell types are of particular interest. For example, attenuated salmonella typhimurium is under study as a candidate vector for oral vaccine delivery (Xiang et al., *Immunol Rev* 222:117, 2008; and Iweala et al., *J Immunol* 183(4):2252, 2009) and engineered *E. coli* bacteria have been shown to be capable of specific homing to poorly oxygenated tumors (Cheong et al., *Science* 314(5803):1308, 2006). Bacteria offer new modes of administration and tissue site targeting possibilities, such as oral administration and the ability to target therapeutics to the gut and gut-associated lymphoid tissues. Such microbial vectors may offer advantages relative to autologous host cells in terms of creating off-the-shelf ready-to-use cell-nanoparticles systems. Particles conjugation to microbes can be achieved using the same suite of chemical strategies described for mammalian cells. In some instances, temporary removal of flagellar coats of microbes (e.g., via simple mechanical shearing as described by Rosu et al., *J Bacteriol* 188(14):5196, 2006) can be used to achieve optimal conjugation of particles to microbe cell bodies.

Methods

Provided herein are methods of producing nanostructures. An example of a nanostructure is a protein nanogel, such as a protein nanogel that contains intact, biologically-active proteins but does not contain a carrier (e.g., albumin, BSA). In some embodiments, a method of producing a carrier-free, biologically-active protein nanogel comprises contacting a protein with a degradable linker under conditions that permit reversible covalent crosslinking of proteins to each other through the degradable linker, thereby producing a carrier-free, biologically-active protein nanogel. In some embodiments, a method further comprises contacting the protein nanogel with a polymer under conditions that permit crosslinking of the polymer to proteins of the protein nanogel, thereby producing a carrier-free, biologically-active protein-polymer nanogel. In some embodiments, a plurality of protein nanogels or a plurality of protein-polymer nanogels is produced.

Typically, conditions that permit reversible covalent crosslinking of proteins to each other through a degradable linker include contacting the proteins with degradable linkers at a temperature of 4° C. to 25° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.). In some embodiments, proteins are incubated with the degradable linkers in an aqueous buffer (e.g., PBS) at a temperature of 4° C. to 25° C. (e.g., room temperature). In some embodiments, proteins are incubated with the degradable linkers in an aqueous buffer (e.g., PBS) at a temperature of no greater than 30° C. In some embodiments, conditions that permit reversible covalent crosslinking of proteins to each other through a degradable linker include contacting proteins with degradable linkers for 30 minutes to two hours, or 30 minutes to one hour (e.g., 30, 35, 40, 45, 50, 55 or 60 minutes). In some embodiments, proteins are incubated with the degradable linkers in an aqueous buffer (e.g., PBS) for 30 minutes to two hours, or 30 minutes one hour.

In some embodiments, the concentration of the protein in the aqueous buffer is 10 mg/mL to 50 mg/mL. For example, the concentration of the protein in an aqueous buffer may be 10 mg/mL, 15 mg/mL, 20 mg/mL, 25 mg/mL, 30 mg/mL, 35 mg/mL, 40 mg/mL, 45 mg/mL or 50 mg/mL protein/aqueous buffer).

In some embodiments, the weight percentage of protein in a carrier-free, biologically-active protein nanogel or protein-polymer nanogel is at least 75% w/w. For example, the weight percentage of protein in the carrier-free, biologically-active protein-polymer nanogels is at least 80% w/w, at least 85% w/w, at least 90% w/w, or at least 95% w/w. In some embodiments, the weight percentage of protein in a carrier-free, biologically-active protein nanogel or protein-polymer nanogel is 75% w/w to 90% w/w, 80% w/w to 90% w/w, or 85% w/w to 90% w/w.

Conditions that permit crosslinking of a polymer to proteins of a protein nanogel include contacting the protein nanogel with a polymer at a temperature of 4° C. to 25° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.). In some embodiments, protein nanogels are incubated with the polymers in an aqueous buffer (e.g., PBS) at a temperature of 4° C. to 25° C. (e.g., room temperature). In some embodiments, protein nanogels are incubated with the polymers in an aqueous buffer (e.g., PBS) at a temperature of no greater than 30° C. In some embodiments, conditions that permit crosslinking of a polymer to proteins of a protein nanogel include contacting the protein nanogel with a polymer for 30 minutes to two hours, or 30 minutes to one hour (e.g., 30, 35, 40, 45, 50, 55 or 60 minutes). In some embodiments, protein nanogels are incubated with the polymer in an aqueous buffer (e.g., PBS) for 30 minutes to two hours, or 30 minutes one hour.

In some embodiments, methods of the present disclosure specifically exclude contacting a protein with a degradable linker in the presence of an organic solvent (e.g., an alcohol such as ethanol or isopropanol). In some embodiments, methods of the present disclosure specifically exclude contacting a protein nanogel with a polymer in the presence of an organic solvent (e.g., an alcohol such as ethanol or isopropanol). Organic solvents may adversely affect the biological activity of the proteins.

Other methods of producing nanostructures of the present disclosure may comprise modifying a protein with a degradable linker and polymerizable functional groups, and polymerizing the polymerizable functional groups with a crosslinker and soluble fluoride.

Figure 3A:
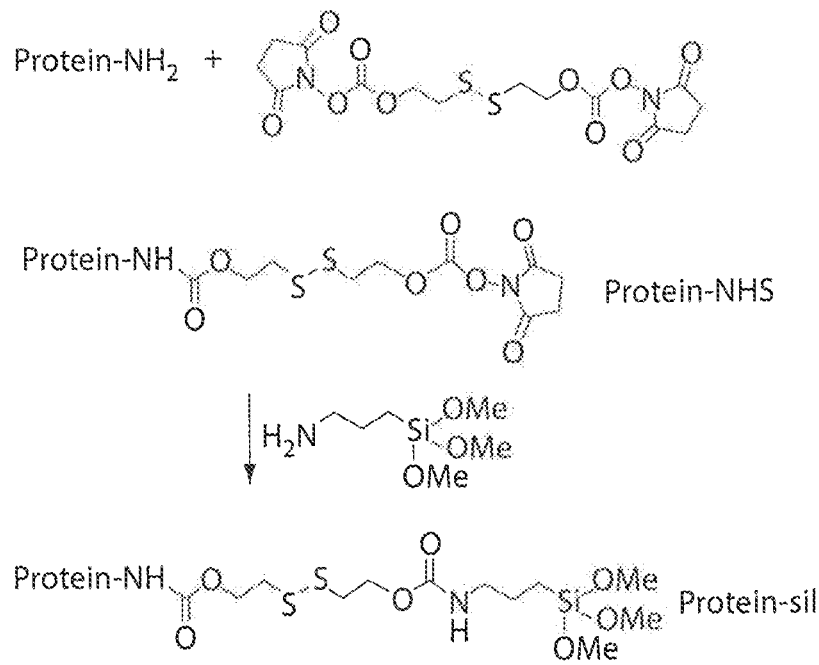
FIGS. 3A-3D show an example of synthesis (FIG. 3A) and MALDI mass spectrum (FIG. 3B) of IL2-fc-silane. Dynamic light scattering (DLS) (FIG. 3C) and scanning electron microscopy (SEM) (FIG. 3D) analysis of the IL2-silica NCs are also shown. IL-2-Fc is a bivalent fusion protein in which the C terminus of murine wild-type IL-2 is linked to a mouse IgG2a Fc domain.

Proteins of the disclosure may be modified with, or conjugated to, a degradable linker such as, for example, a redox responsive linker. The modification may, in some embodiments, be a covalent modification. FIG. 3A illustrates one example of a protein modification scheme. In this example, a protein is covalently conjugated, through a degradable linker, to silane.

Polymerizable functional groups may be polymerized with a crosslinker in the presence of a soluble fluoride catalyst. In some embodiments, the crosslinker is a polymer (e.g., silane-PEG-silane). In some embodiments, the soluble fluoride is sodium fluoride. In some embodiments, the soluble fluoride is potassium fluoride.

The disclosure also provides methods of administering protein conjugates and nanostructures in vivo to subjects.

The methods of the disclosure can be practiced in virtually any subject type that is likely to benefit from delivery of proteins as contemplated herein. Human subjects are preferred subjects in some embodiments. Subjects also include animals such as household pets (e.g., dogs, cats, rabbits, ferrets), livestock or farm animals (e.g., cows, pigs, sheep, chickens and other poultry), horses such as thoroughbred horses, laboratory animals (e.g., mice, rats, rabbits), and the like. Subjects also include fish and other aquatic species.

The subjects to whom protein conjugates are delivered may be normal, or healthy, subjects. Alternatively they may have or may be at risk of developing a condition that can be diagnosed or that can benefit from delivery of one or more particular proteins.

Such conditions include cancer (e.g., solid tumor cancers), autoimmune disorders, allergies or allergic conditions, asthma, transplant rejection, and the like.

Tests for diagnosing various conditions embraced by the present disclosure are known in the art and will be familiar to the ordinary medical practitioner. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject having a cancer is a subject who has detectable cancer cells. A subject at risk of developing a cancer is a subject who has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (e.g., carcinogens) such as tobacco, asbestos, or other chemical toxins, and subjects previously treated for cancer and in apparent remission.

Cancer

The present disclosure contemplates administration of reversibly modified protein conjugates and/or protein nanostructures to subjects having or at risk of developing a cancer including, for example, a solid tumor cancer. The cancer may be carcinoma, sarcoma or melanoma. Carcinomas include, without limitation, to basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system. Other cancers are known and are contemplated herein.

Sarcomas are rare mesenchymal neoplasms that arise in bone (osteosarcomas) and soft tissues (fibrosarcomas). Sarcomas include without limitation liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., not bone) Ewing's sarcoma, and primitive neuroectodermal tumor), synovial sarcoma, angiosarcomas, hemangiosarcomas, lymphangiosarcomas, Kaposi's sarcoma, hemangioendothelioma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), and chondrosarcoma.

Melanomas are tumors arising from the melanocytic system of the skin and other organs. Examples of melanoma include without limitation lentigo maligna melanoma, superficial spreading melanoma, nodular melanoma, and acral lentiginous melanoma.

The cancer may be a solid tumor lymphoma. Examples include Hodgkin's lymphoma, Non-Hodgkin's lymphoma, and B cell lymphoma.

The cancer may be, without limitation, bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, prostate cancer, retinoblastoma or rhabdomyosarcoma.

Compositions

Compositions, including pharmaceutical compositions, comprising protein nanostructures (e.g., protein nanogels) are provided herein. A composition can be administered to a subject in pharmaceutically-acceptable amounts and in pharmaceutically-acceptable compositions. The term "pharmaceutically acceptable" means a non-toxic material that does not interfere with the effectiveness of the biological activity of the active ingredients (e.g., biologically-active proteins of the nanostructures). Such compositions may, in some embodiments, contain salts, buffering agents, preservatives, and optionally other therapeutic agents.

Pharmaceutical compositions also may contain, in some embodiments, suitable preservatives.

Pharmaceutical compositions may, in some embodiments, be presented in unit dosage form and may be prepared by any of the methods well-known in the art of pharmacy.

Pharmaceutical compositions suitable for parenteral administration, in some embodiments, comprise a sterile aqueous or non-aqueous preparation of the nanostructures, which is, in some embodiments, isotonic with the blood of the recipient subject. This preparation may be formulated according to known methods. A sterile injectable preparation also may be a sterile injectable solution or suspension in a non-toxic parenterally-acceptable diluent or solvent.

Pharmaceutical compositions of the present disclosure are administered, in some embodiments, by a conventional route, including injection or by gradual infusion over time. Administration may, for example, be oral, intravenous, intraperitoneal, intramuscular, intracavity, intratumor, or transdermal.

Pharmaceutical compositions of the present disclosure are administered, in some embodiments, in effective amounts. An "effective amount" is that amount of any of the nanostructure provided herein that alone, or together with further doses and/or other therapeutic agents, produces a desired response (e.g., pseudoautocrine stimulation, augment T cell expansion and minimize systemic side effects of adjuvant drugs in vivo).

Pharmaceutical compositions of the present disclosure, in some embodiments, may be sterile and contain an effective amount of a nanostructure (e.g., nanogel), alone or in combination with another agent, for producing the desired response in a unit of weight or volume suitable for administration to a subject (e.g., human subject). The response can, for example, be measured by determining the physiological effects of the nanostructure composition.

The doses of compositions administered to a subject may be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that subject/patient tolerance permits.

EXAMPLES

Example 1

In the context of adoptive T cell therapy for cancer treatment, adjuvant cytokine drug, IL 2, provides key adjuvant signals to donor T cells but also elicits severe dose-limiting inflammatory toxicity and expands regulatory T cells ($T_{reg}$s). Provided herein is a delivery method to safely and efficiently target IL-2 to therapeutic cells with minimal toxicity.

Figure 2:
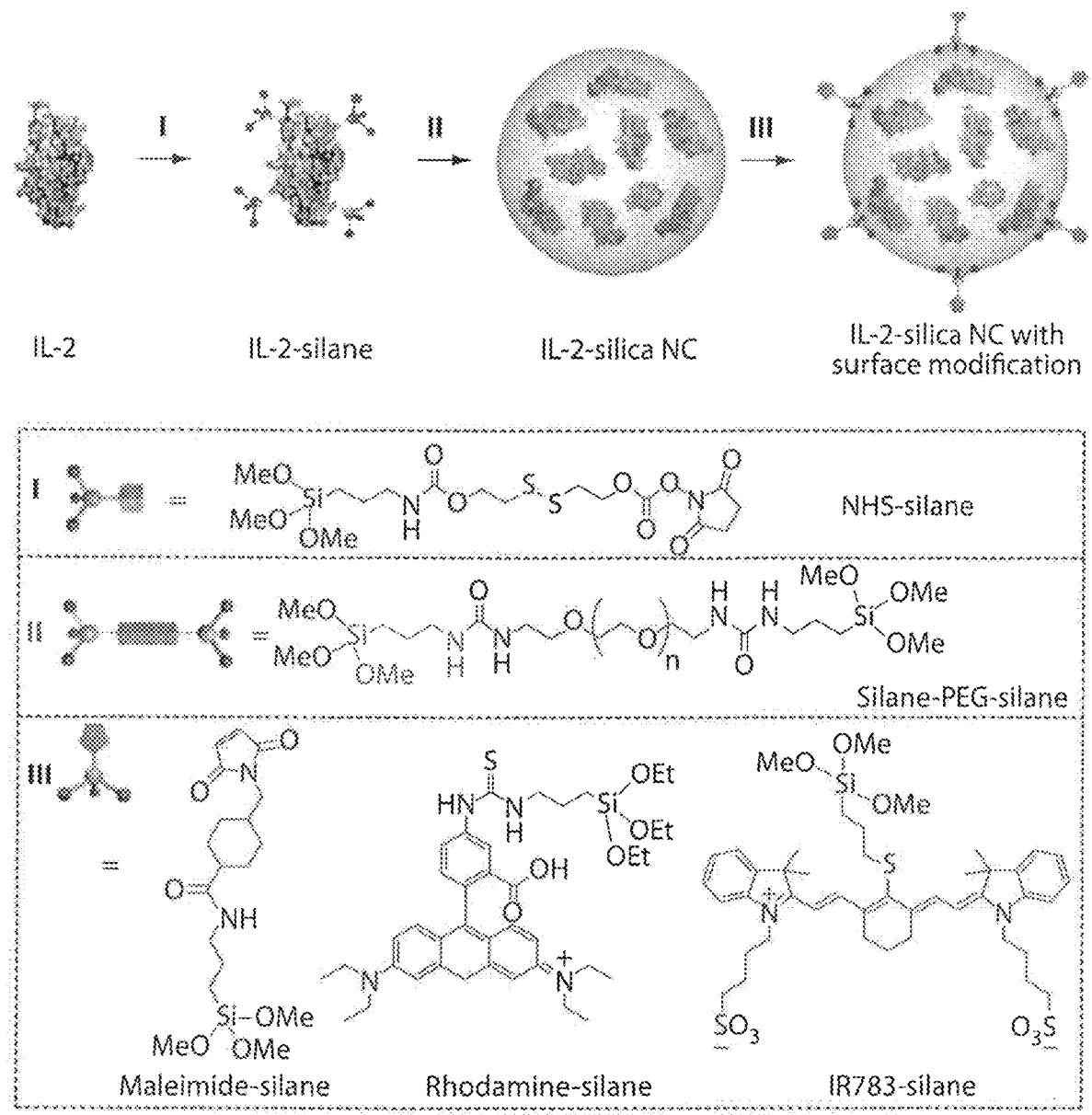
FIG. 2 shows a schematic of an example of synthesis and surface functionalization of IL2-silica NCs.

FIG. 1 illustrates an example of a method of preparing protein-silica nanocapsules (NCs). Polymerizable silane groups were first conjugated to IL-2 through a redox responsive linker (Formula I) to prepare IL-2-silane (FIG. 2, I). The modified IL-2 was further reacted with (3-Aminopropyl) triethoxysilane to functionalize IL-2 with polymerizable silane group on the protein surface. Subsequent polymerization of the silane groups together with a crosslinker (e.g., silane-PEG-silane, FIG. 2, II), catalyzed by NaF, resulted in the proteins being wrapped in a degradable silica nanocapsules (NC), which efficiently protects the protein from degradation in physiological conditions. Upon dissolution of the silica NC and cleavage of the linker between the protein and silane groups in physiological conditions, the protein is released to its original form (FIG. 4B).

Methods

The linker of Formula I (109 µg, 50 equiv. of protein) dissolved in 21.8 DMSO was added to IL-2-fc (500 µg) solution in 478 µL PBS buffer. The mixture was rotated at 4° C. for 3 hours. Modified IL-2-fc was washed with PBS (15 mL×3) using a Millipore Amicon ultra-centrifugal filter (molecular weight cutoff=10,000 Da). Purified IL-2-fc-linker conjugate in 500 µL PBS was mixed with (3-aminopropyl) triethoxysilane (55.2 µg, 50 equiv. of protein) and rotated at 4° C. for 3 hours. The resultant silane functionalized IL-2-fc was washed with PBS (15 mL×3) using Millipore Amicon ultra-centrifugal filter to remove unreacted small molecules. IL2-fc-silane dissolved in 500 µL was then mixed with silane-PEG-silane (100 µg, FIG. 2, II) followed by the addition of sodium fluoride (200 µg). The mixture was stirred at 4° C. overnight. The resultant IL-2-fc-silica NCs were washed with PBS (15 mL×3) using ultra-centrifugal filter. The incorporation efficiency of IL-2-fc was determined by centrifuging down the NCs and measuring the concentration of IL-2 in the supernatant using ELISA kit. The loading of IL-2-fc in the final IL-2-fc-NC was calculated based on the incorporation efficiency of IL-2-fc and assuming all the silane-PEG-silane is reacted and in the final NCs.

Figure 3B:
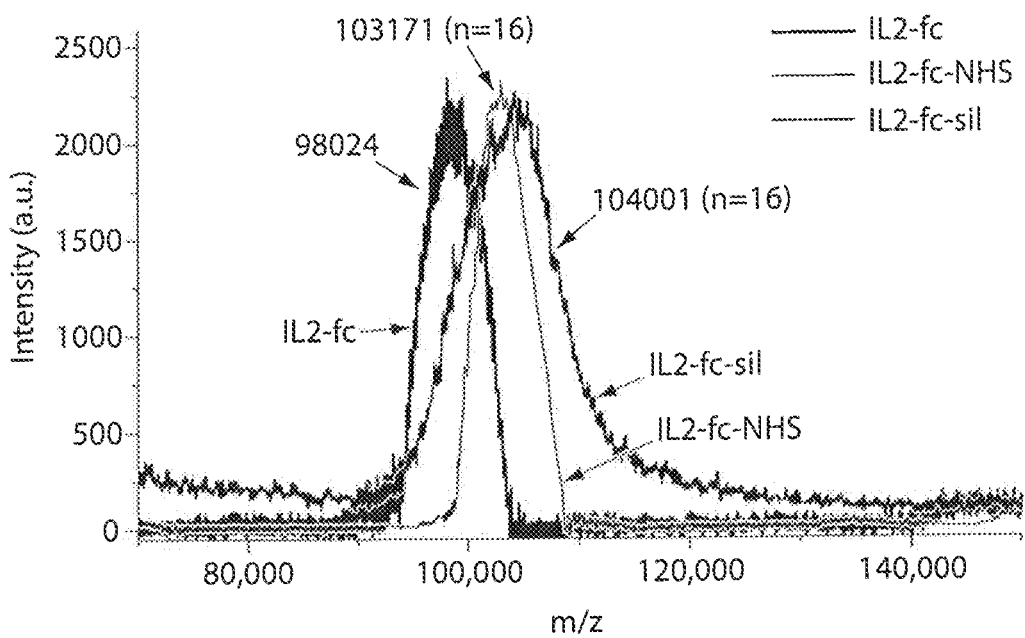
Figure 3C:
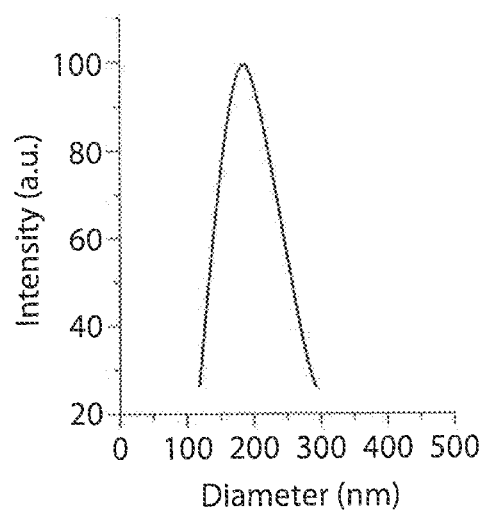
Figure 3D:
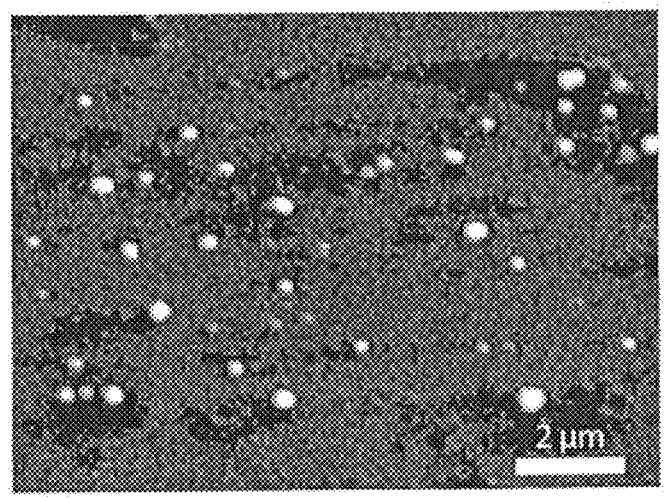

The successful conjugation of silane groups to IL-2 was demonstrated by matrix-assisted laser desorption/ionization (MALDI) analysis (FIG. 3B). The degree of modification of IL-2 can be measured by calculating the increased molecular weight. The results indicate that about 16 lysine residues of IL-2 were covalently attached with silane groups (FIG. 3B). The prepared IL-2-silica NCs was 222.5±5.2 nm in diameter, as shown in both dynamic light scattering (DLS) and scanning electron microscope (SEM) characterization (FIGS. 3C and 3D). Extraordinarily high incorporation efficiency (e.g., 95.5%) and high protein drug loading (e.g., 84.0%) was achieved using this reversible covalent modification method (FIG. 4A). By comparison, an encapsulation method of the prior art typically results in less than 10% incorporation efficiency and ~1% drug loading.

The triggered release of IL-2 from the IL-2-silica NCs was verified by incubating IL-2-silica NCs in buffer of different pH at 37° C. and analyzing the release kinetics of IL-2 with or without reductant reagent, dithiothreitol (DTT). At pH 7.4, addition of 10 mM DTT resulted in 2.6 times faster release of IL-2 over 48 h incubation relative to release without reductant reagent, demonstrating the redox responsive release of IL-2 (FIG. 4C). When the NCs were incubated in buffer with a pH of 9.0, which facilitates the degradation of the silica shell, the release of IL-2 was accelerated (FIG. 4C). These findings demonstrate that IL-2 was effectively conjugated to a reductant cleavable bond and protected by a silica shell.

Figure 5A:
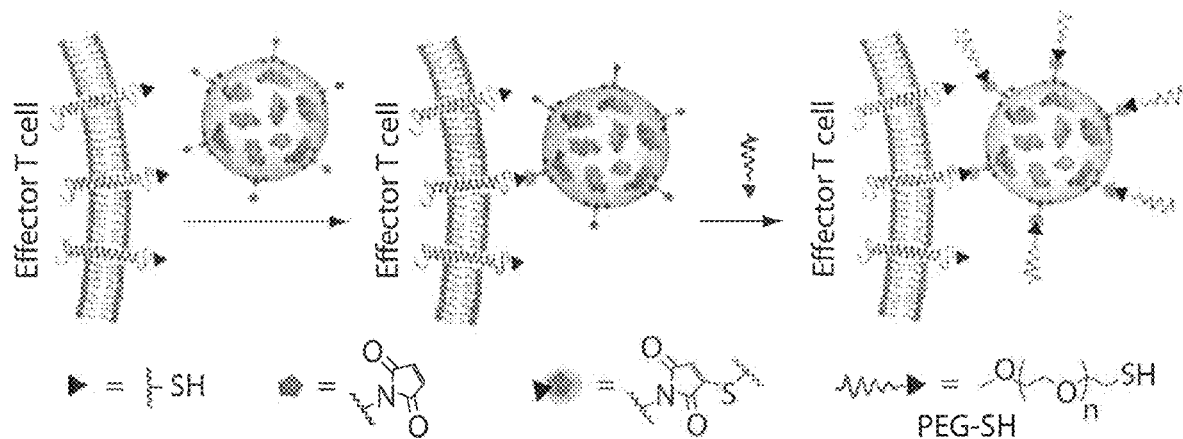
FIG. 5A shows a schematic of chemical conjugation of a maleimide functionalized IL-2-fc-silica NCs to an effector T cell surface via a maleimide-thiol coupling reaction.
Figure 5B:
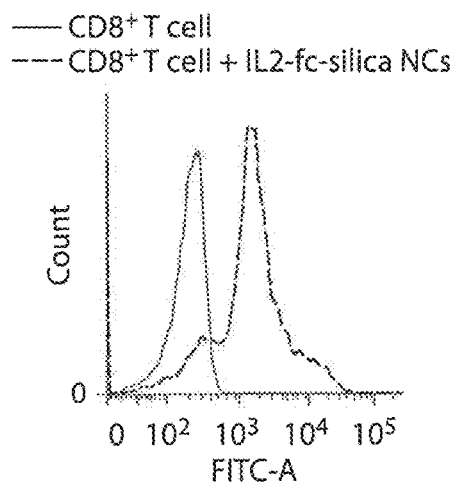
FIG. 5B shows a flow cytometry analysis of T cells with surface-conjugated IL-2-silica NCs.

To stimulate the adoptive transferred T cells specifically and efficiently, IL-2-silica NCs were conjugated directly onto the plasma membrane of donor cells, enabling continuous pseudoautocrine stimulation of transferred cells in vivo (FIG. 1). The silica NCs prevent the degradation of IL-2 by proteases and allow for sustained local release of IL-2 in physiological conditions to expand cytotoxic T cells specifically without activating bystander T cells or expanding Tregs, thus avoiding the serious systemic toxicity of high-dose IL-2. IL-2-silica NCs were first functionalized with maleimide groups using silane chemistry (FIG. 2, III). The maleimide functionalized IL-2-silica NCs were then covalently attached to the surface of adoptive transferred T cells through a maleimide-thiol reaction (FIG. 5A). Residual maleimide groups of the NCs were quenched by in situ conjugation of thiol-terminated polyethylene glycol (PEG-SH, Mw=5 kDa) (FIG. 5A). The successful cell surface conjugation was evidenced by flow cytometry analysis of the T cells with surface bound fluorescence dye labeled IL-2-silica NCs (FIG. 5A).

Figure 5C:
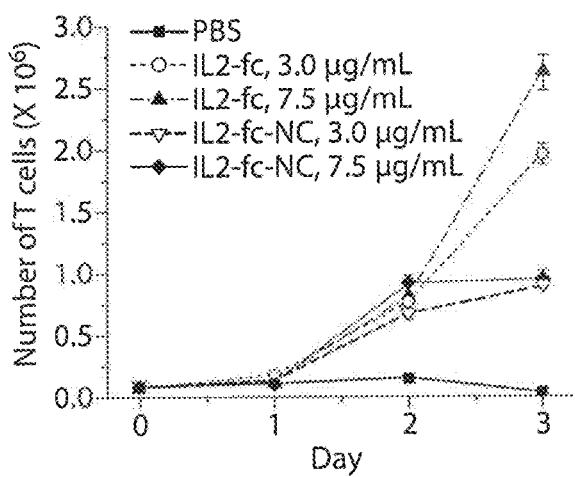
FIGS. 5C and 5D show an in vitro CD8+ T cell proliferation assay with free IL2-fc or IL2-fc-NC by manual counting and flow cytometry, respectively.
Figure 5D:
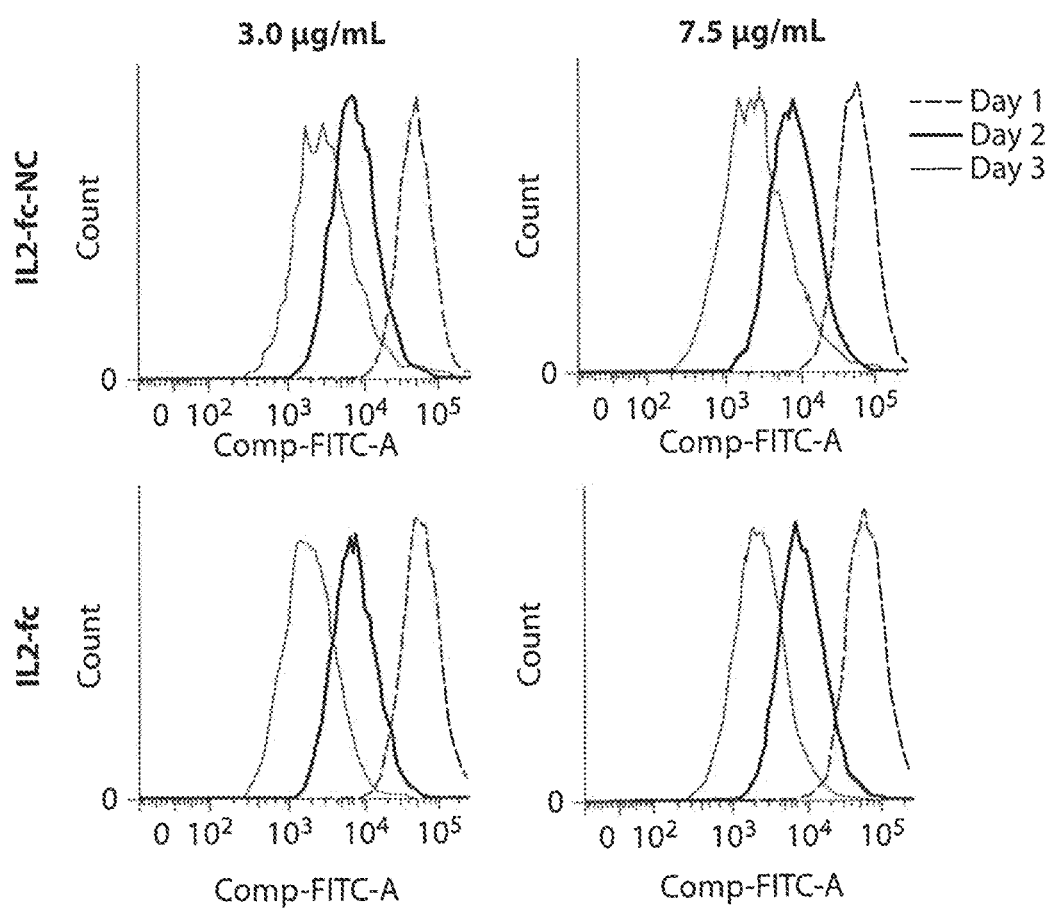

To evaluate whether the surface bond IL-2-silica NCs could release IL-2 with retained biological activity and expand CD8+ T cells in vitro, purified CD8+ T cells from splenocytes of mice were treated with free IL-2, or conjugated with IL-2-silica NCs of equivalent amount of IL-2, and then co-cultured with CD3CD28 beads of 1:1 ratio. Cell proliferation was monitored by both manual counting and analyzing carboxyfluorescein (CFSE) dilution by flow cytometry (FIGS. 5C and 5D). At two concentrations tested (3.0 μg/mL or 7.5 μg/mL), surface bond IL-2-silica NCs induces the comparable level of T cells expansion with free IL-2 until day 3.

Figures 6A, 6B:
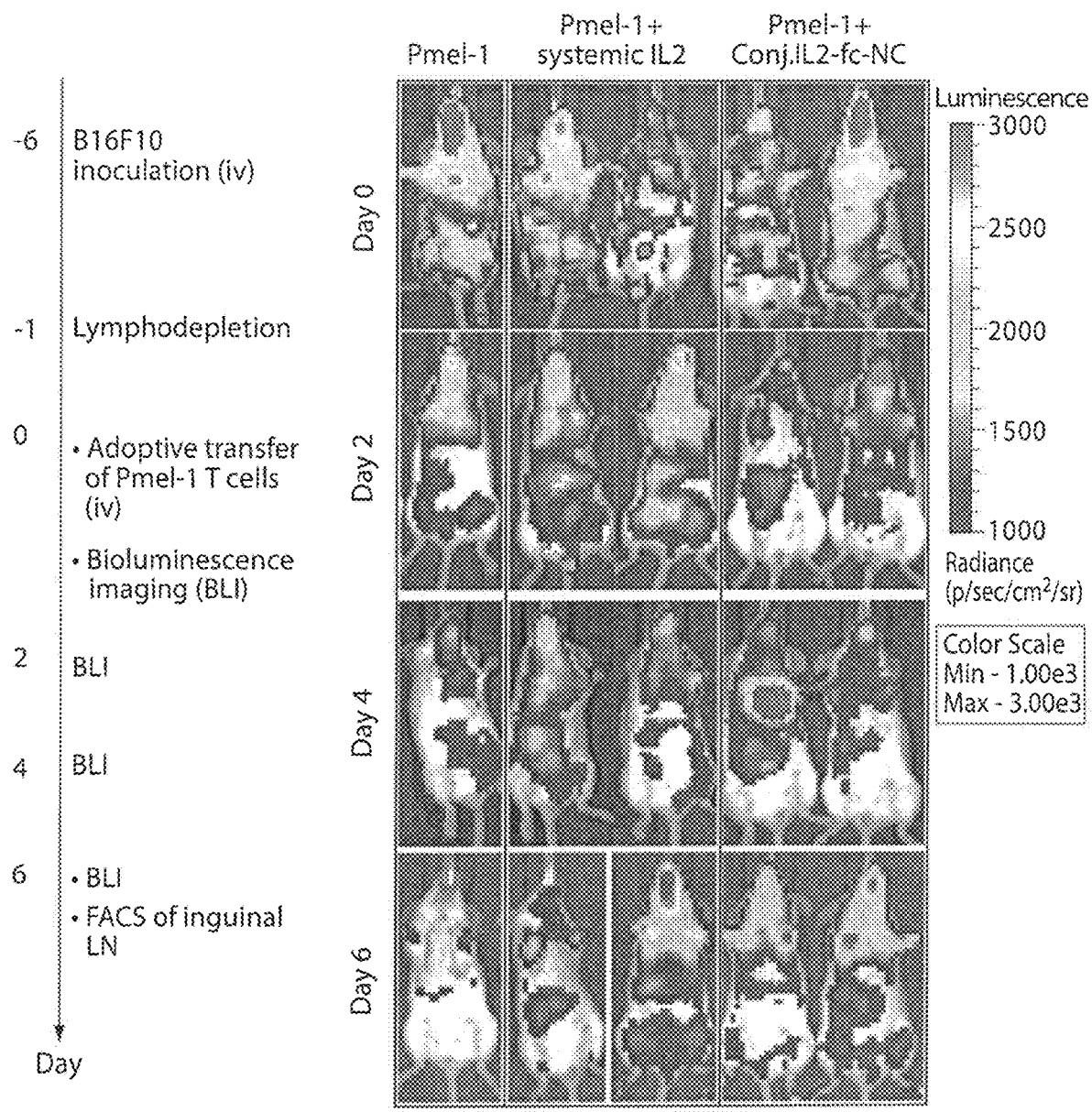
FIG. 6A shows a timeline of an in vivo CD8+ T cells expansion study.
FIG. 6B shows images of mice with established lung metastases of B 16F10 melanoma received adoptive transfer of luciferase-expressing Pmel-1 melanoma-specific CD8+ T-cells. T-cell expansion was followed over time by bioluminescence imaging.
Figure 6C:
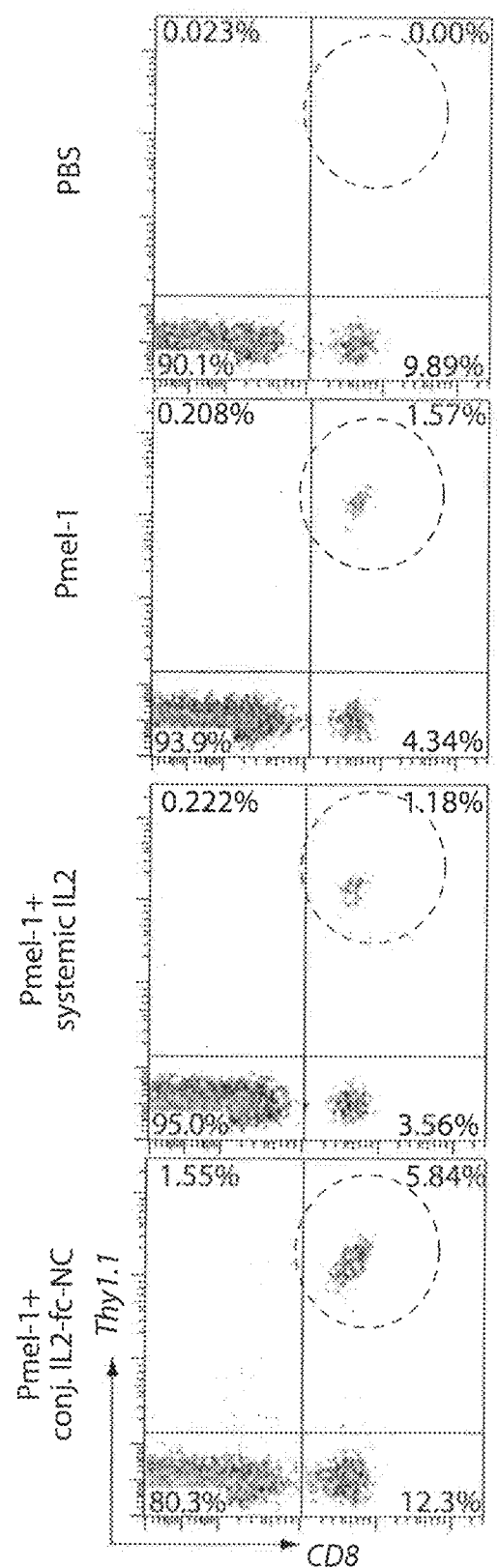
FIG. 6C shows a flow cytometry analysis of the frequency of adoptively-transferred T-cells in the inguinal lymph nodes on day 6 after adoptive transfer.

To further test the potential functional impact of stimulatory IL-2-silica NCs in vivo, the response of Pmel-1 melanoma specific T-cells was assessed in vivo during adoptive transfer treatment of B 16F10 tumors in a murine metastatic lung tumor model. B 16F10 melanoma cells were injected through the tail vein to allow lung metastases to establish for 6 days. Animals were then lympho-depleted and received adoptive transfer of luciferase-expressing Pmel-1 melanoma-specific CD8+ T-cells with no further treatment, free IL-2 or surface-conjugated IL-2-silica NCs, respectively in each group. T-cell expansion was followed over time by bioluminescence imaging. Adoptively-transferred cells, without further adjuvant support, showed a low level persistence in the tumor-bearing recipients, which gradually declined over 6 days, as expected in the absence of additional stimulation or protection from tumor immunosuppression (FIG. 6B). To assess the relative potency of stimulation achieved by surface-conjugated IL-2-silica NCs compared to traditional systemic IL-2 therapy, the expansion of T-cells following injection of soluble IL-2 was compared to the expansion of T-cells with surface-conjugated IL-2-silica NCs (at an equivalent total amount of IL-2). T cells with surface-conjugated IL-2-silica NCs expanded to a higher level on day 4 and day 6 relative to the T-cells with soluble IL-2 injection (FIG. 6B). Flow cytometry analysis of T-cells pooled from the inguinal lymph nodes on day 6, after adoptive transfer, confirmed that the frequency of tumor-specific CD8+ T-cells (pmel-1 T-cells express Thy1.1) was nearly 5 times greater in mice that received T-cells with surface-conjugated IL-2-silica NCs relative to T-cells with soluble IL-2 (FIG. 6B). Soluble IL-2 showed no enhancement in T-cell expansion compared to the injection of T cells alone. Thus, surface-conjugated IL-2-silica NCs resulted in enhanced and more sustained T-cells expansion in tumor bearing mice compared with soluble IL-2.

Example 2

Figure 8A:
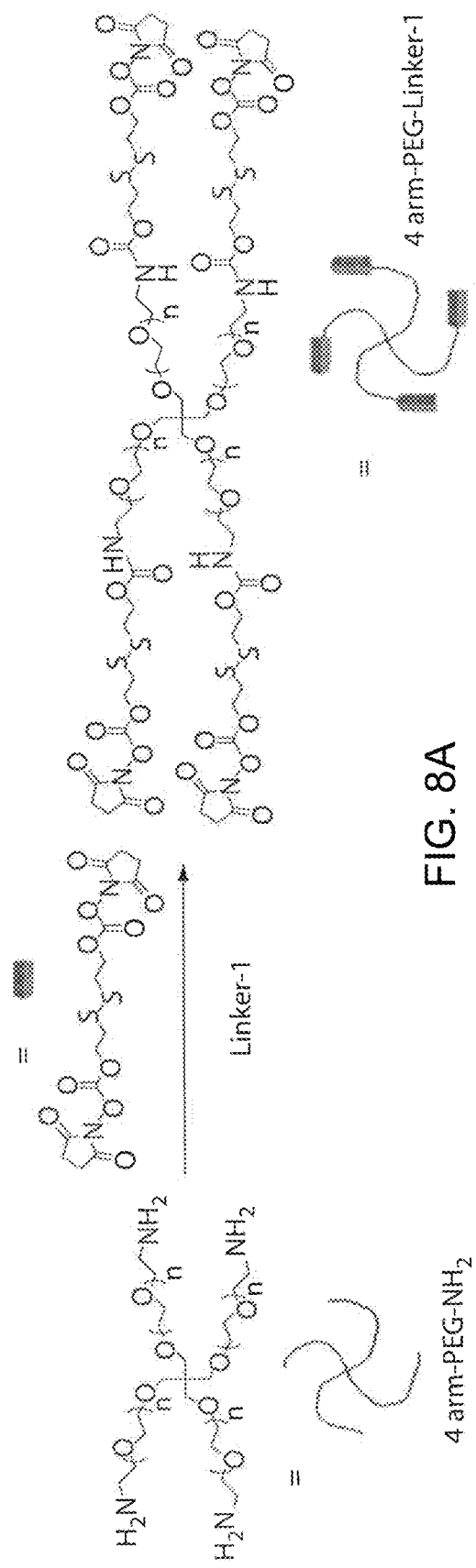
FIGS. 8A-8B show schematics of the preparation of protein-PEG nanogels (NGs).

Linker-1 was first conjugated to the end of a 4 arm-PEG polymer chain (FIG. 8A). A subsequent crosslinking reaction of 4 arm-PEG-Linker-1 and IL-2-fc in PBS buffer resulted in protein-PEG nanogel particle formation (FIG. 8B), which efficiently protects the protein from degradation in physiological conditions. Upon reductant dependent cleavage of the linker between the protein and PEG in physiological conditions, the protein is released to its original form.

Methods

FIG. 8A: Synthesis of 4 arm-PEG-Linker-1. 4 arm-PEG-NH2 (10 mg) dissolved in 300 μL tetrahydrofuran (THF) was added drop-wise to an 800 μL THF solution of Linker-1 (17.4 mg, 40 equiv.) and triethylamine (5 μL). The mixture was further stirred at room temperature overnight. Four-arm-PEG-Linker-1 was purified by dialysis (molecular weight cutoff=3,000 Da).

Figure 8B:
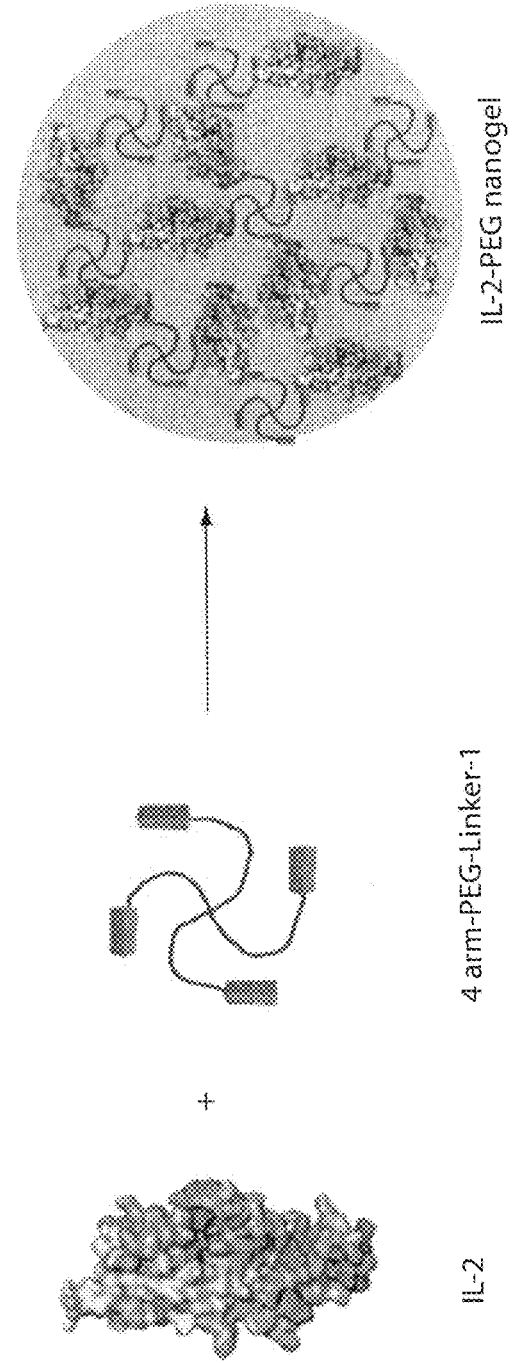

FIG. 8B: IL2-fc-PEG nanogel particle formation. IL-2-fc (50 μg) was mixed with 4 arm-PEG-Linker-1 (15 μg, 3 equiv.) in 100 μL PBS buffer and rotated at 4° C. overnight. The resultant IL2-fc-PEG nanogel was washed with PBS (15 mL×3) using Millipore Amicon ultra-centrifugal filter (molecular weight cutoff=100,000 Da) to remove unreacted IL-2-fc or 4 arm-PEG-Linker-1. The incorporation efficiency of IL-2-fc was determined by centrifuging down the nanogels and measuring the concentration of IL-2-fc in the supernatant. The loading of IL-2-fc in the final IL2-fc-PEG nanogel (NG) was calculated based on the incorporation efficiency of IL-2-fc and assuming all 4 arm-PEG-Linker-1 is reacted and in the final nanogels.

The formation of IL2-fc-PEG nanogel particles was demonstrated by DLS measurement. The as prepared IL2-fc-PEG nanogel was 226.8±8.4 nm in diameter.

Example 3

Preparation and Characterization of Protein Nanogel (NG)

As shown in FIG. 9, IL2-Fc (100 μg) was mixed with a disulfide crosslinker (4.36 μg, 10 equiv.) in 10 μL of phosphate buffered saline (PBS) and incubated at room temperature for 1 hour (h). The resultant IL2-Fc-crosslinked nanogel was washed with PBS (0.4 mL×3) using Millipore Amicon ultra-centrifugal filter (molecular weight cutoff=100,000 Da) to remove unreacted IL2-Fc and/or unreacted disulfide crosslinker. The IL2-Fc-crosslinked nanogel was then PEGylated by mixing the IL2-Fc-crosslinked nanogel with 4 arm-PEG10k-NH2 (FIG. 9A; 50 μg, 5 equiv.) in 100 μL PBS buffer. The mixture was incubated at room temperature for 0.5 h. The PEGylated IL2-Fc-crosslinked nanogel was then washed with the ultra-centrifugal filter. The incorporation efficiency of IL2-Fc was determined by centrifuging down the PEGylated IL2-Fc-crosslinked nanogels and measuring the concentration of IL2-Fc in the supernatant.

The PEGylated IL2-Fc-crosslinked nanogel was analyzed with HPLC equipped with a size exclusion column (FIG. 10A). By comparison with free IL2-Fc, the shift of the peak indicates the formation of crosslinked protein with much a larger molecular weight. The PEGylated IL2-Fc-crosslinked nanogel was further analyzed with transmission electron microscopy (TEM; FIG. 10B) and dynamic light scattering (DLS; FIG. 10C) to characterize the size and morphology of the nanogels. The TEM image in FIG. 10B shows that the size of PEGylated IL2-Fc-crosslinked nanogel as a dry solid is ~50-60 nm in diameter. The DLS characterization of the PEGylated IL2-Fc-crosslinked nanogel in PBS solution indicated that the hydrodynamic size of nanogel is ~85.6 nm. The larger hydrodynamic size relative to the size as a dry solid is due to the hydration of surface PEG on the PEGylated IL2-Fc-crosslinked nanogel.

Figure 11A:
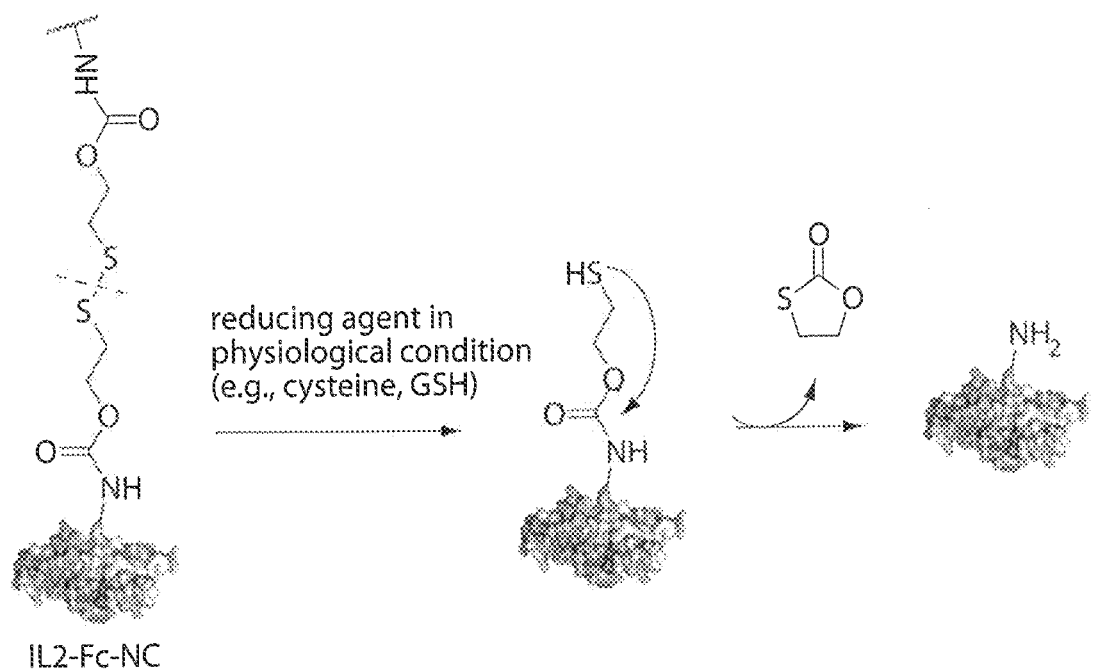
FIG. 11A shows a schematic of a mechanism of the release of intact, biologically-active protein from a protein nanogel.
Figure 11B:
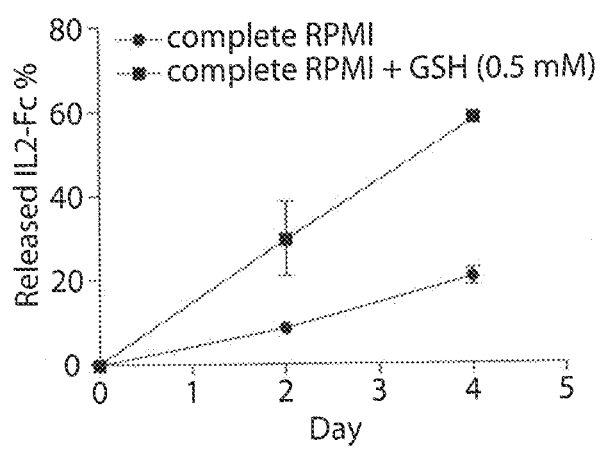
FIG. 11B shows a graph of release kinetics of IL-2-Fc from a protein nanogel.
Figure 11C:
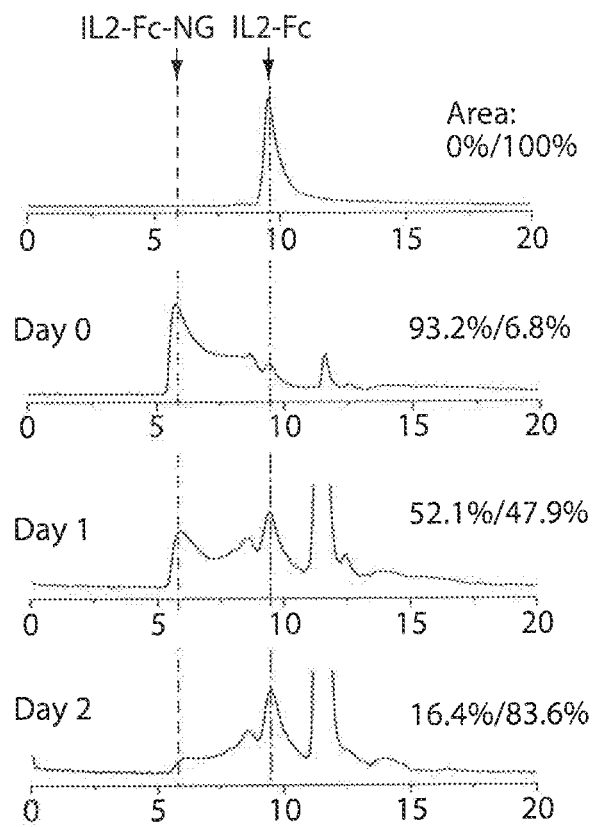
FIG. 11C shows glutathione (GSH) facilitated release of IL2-Fc, verified by HPLC equipped with a size exclusion column.
Figure 11D:
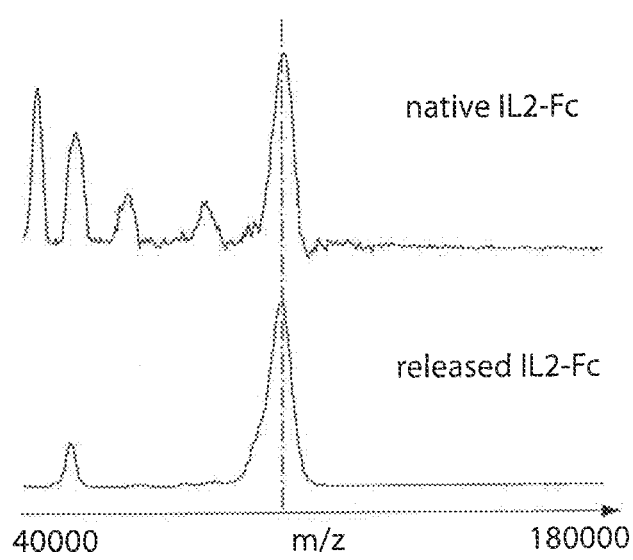
FIG. 11D shows the released IL2-Fc and native IL2-Fc, analyzed with mass spectrum of Matrix-assisted laser desorption/ionization.

The PEGylated IL2-Fc-crosslinked nanogel can release intact IL2-Fc in physiological condition. FIG. 11A, without being bound by, schematizes a release mechanism of the IL2-Fc from NG without any chemical residues remaining on the protein molecule. FIG. 11B shows controlled sustained release of IL2-Fc in complete Roswell Park Memorial Institute (RPMI) media (media for T cells in vitro). When glutathione (GSH), a reducing agent in physiological condition, was added, the release kinetics was accelerated. The released mixture was also characterized with HPLC as shown in FIG. 11C: the peak of crosslinked IL2-Fc NG decreased, while the peak for free IL2-Fc increased over time. The released IL2-Fc was also characterized with matrix-assisted laser desorption/ionization (MALDI) mass spectroscopy to demonstrate that the released IL2-Fc has the same molecular weight as the native IL2-Fc, indicating that no chemical residue remained the IL2-Fc molecule.

Figure 12A:
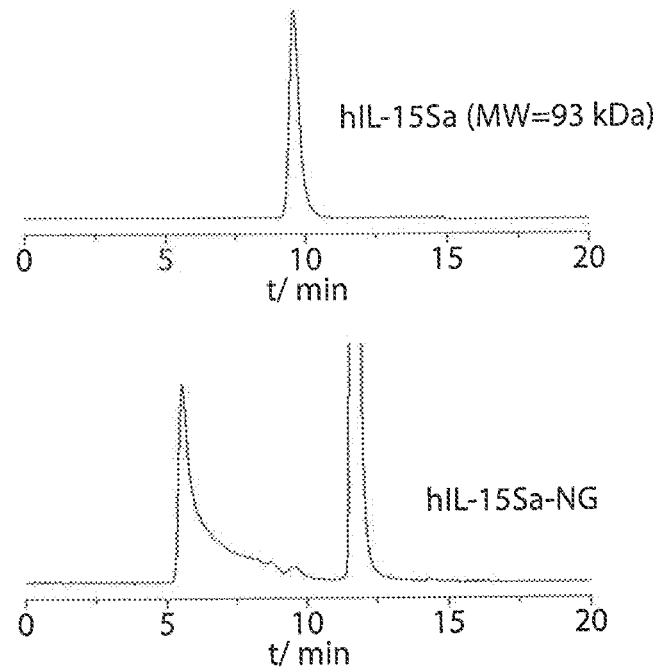
FIGS. 12A-12B show the formation of other protein nanogels. Analyses of the human IL-15 superagonist (hIL-15Sa) nanogel (FIG. 12A) and native mouse IL-2 (mIL-2) nongel (FIG. 12B) with HPLC equipped with a size exclusion column are shown.
Figure 12B:
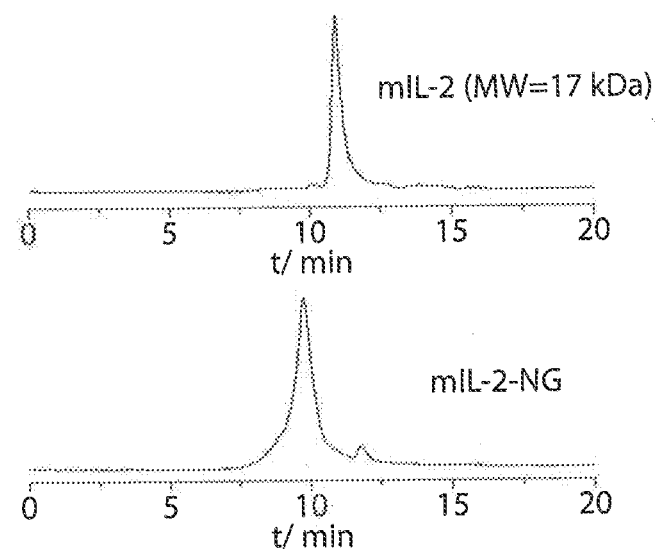

Similar protein nanogels can be formulated using therapeutic proteins other than IL-2-Fc. For example, human IL-15 superagonist (hIL-15Sa)-crosslinked and native mouse IL-2 (mIL-2)-crosslinked nanogels are represented by HPLC curves in FIG. 12.

Figure 13:
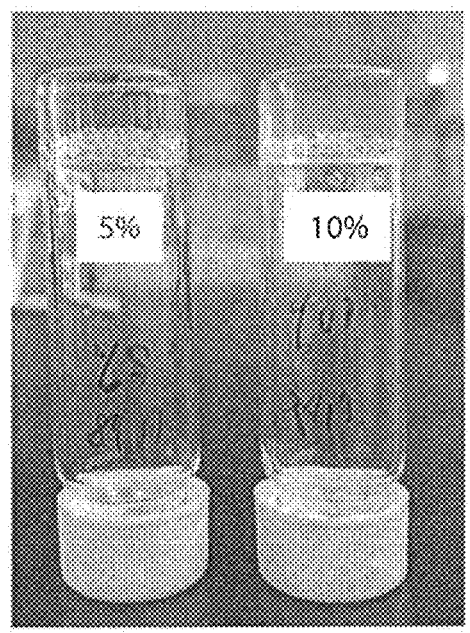
FIG. 13 shows an image of vials containing bulk gel instead of nanogels when the protein concentration is too high (≥50 mg/mL).

At protein concentrations of greater than 50 mg/mL, bulk gel formed instead of nanogel (FIG. 13).

Example 4

Figure 14A:
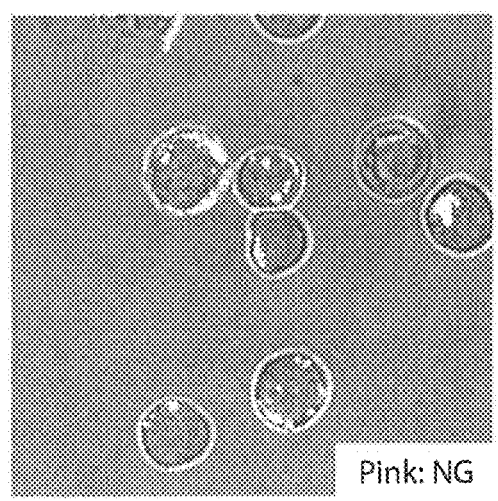
FIG. 14A shows a confocal microscope image of T cells with surface-conjugated protein nanogels.
Figure 14B:
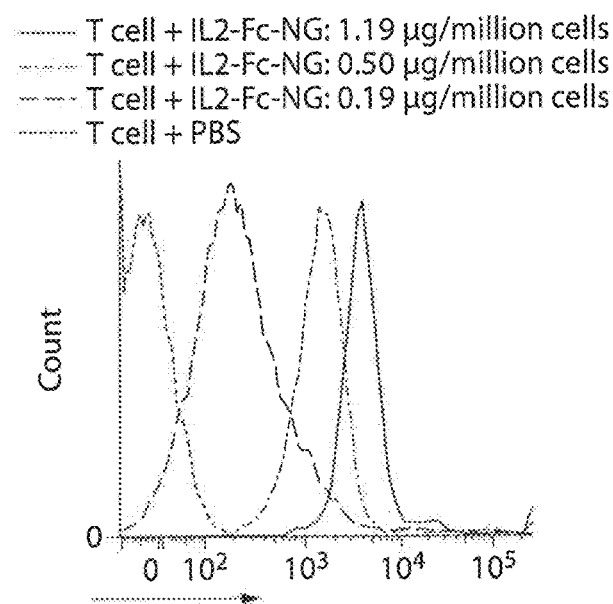
FIG. 14B shows a flow cytometry graph of controlled conjugation of IL-2-Fc nanogel to T cell surface at different amounts.

Carrier Free Delivery of a Cytokine Using a Protein Nanogel to Augment T Cells for Adoptive Cell Therapy for Cancer To demonstrate the application of a protein nanogel of the present disclosure, in the context of adoptive T cell transfer (ACT) for cancer immunotherapy, a IL2-Fc-crosslinked nanogel was used to deliver IL2-Fc to specifically expand adoptive transferred T cells in vivo. An IL2-Fc-crosslinked nanogel provides a highly efficient way to deliver a sufficient amount of the cytokine to the T cell surface through conjugation. An IL2-Fc-crosslinked nanogel was surface modified with a disulfide crosslinker (*Nat. Med.* 16, 1035-1041, 2010, incorporated by reference herein; FIG. 9) and then conjugated to the surface of effector T cells. As shown in FIG. 14A, the IL2-Fc-crosslinked nanogel can be conjugated to the surface of T cells. By controlling the amount of IL2-Fc-crosslinked nanogels added to the T cells, the T cell surface density could be well controlled, as evidenced by flow cytometry analysis using fluorescently-labeled IL2-Fc-crosslinked nanogels (FIG. 14B).

Figure 15A:
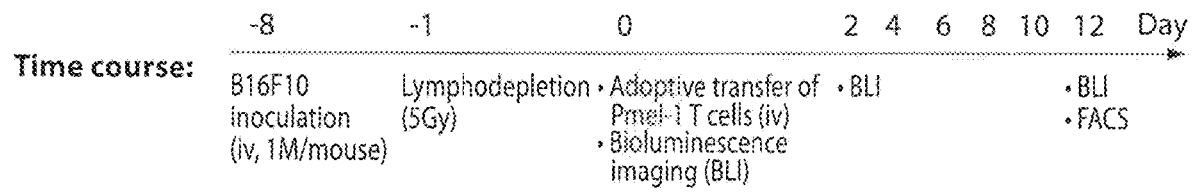
FIGS. 15A-15C show in vivo CD8+ T cells expansion.
Figure 15B:
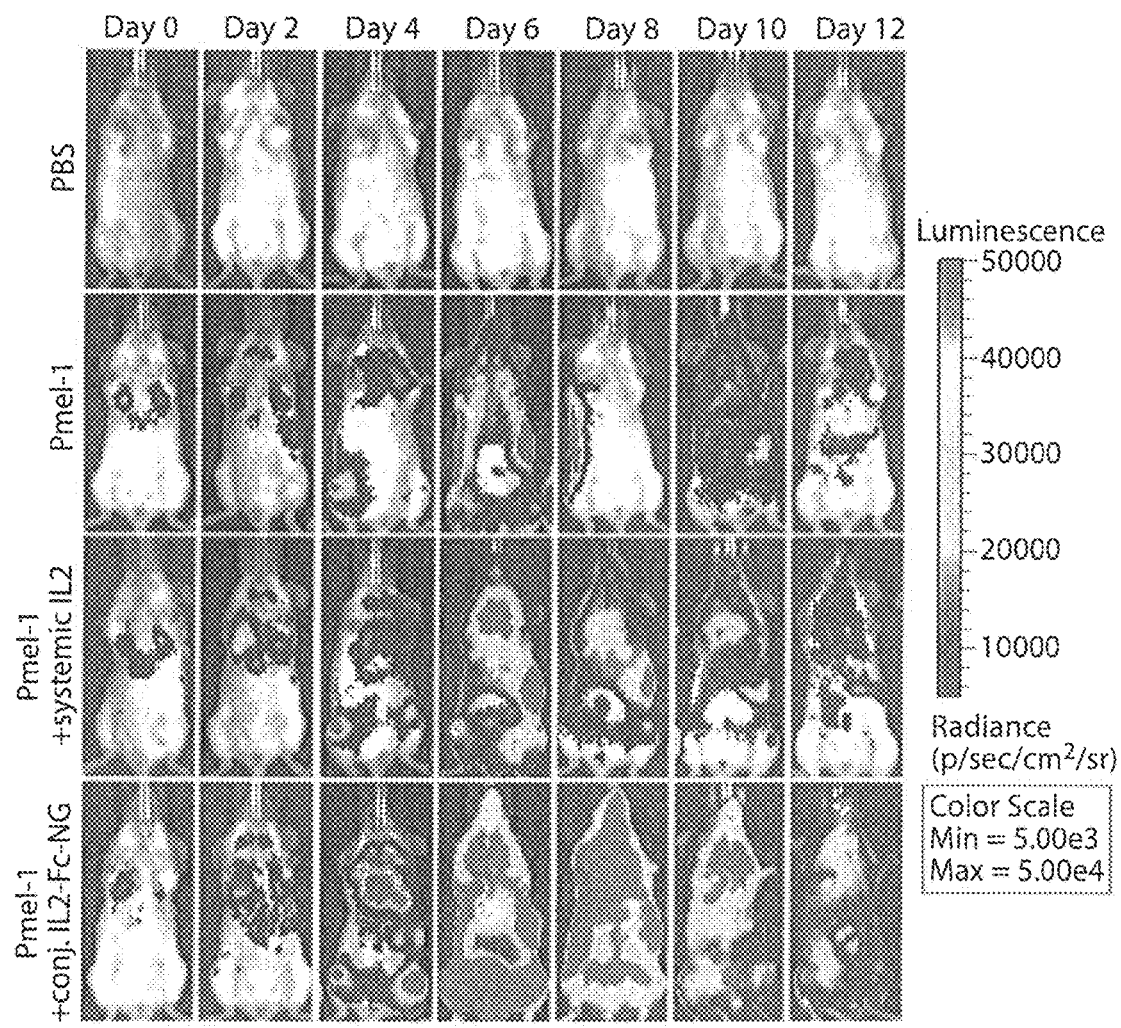
Figure 15C:
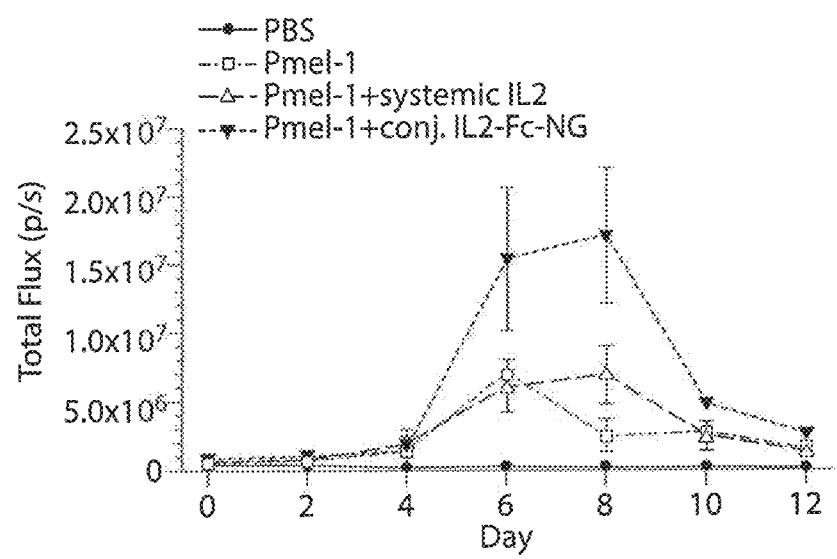

The Pmel-1 melanoma-specific $CD8^+$ T-cells with surface-conjugated IL2-Fc-crosslinked nanogels was adoptive transferred to mice with established lung metastases of B16F10 melanoma. The in vivo expansion of the transferred T cells was monitored over time using bioluminescence imaging. The $CD8^+$ T-cells with surface-conjugated IL2-Fc-crosslinked nanogels showed markedly increased in vivo expansion relative to T cell-only controls or T cells with systemically administered free IL2-Fc (FIGS. 15A-15B).

Figure 16:
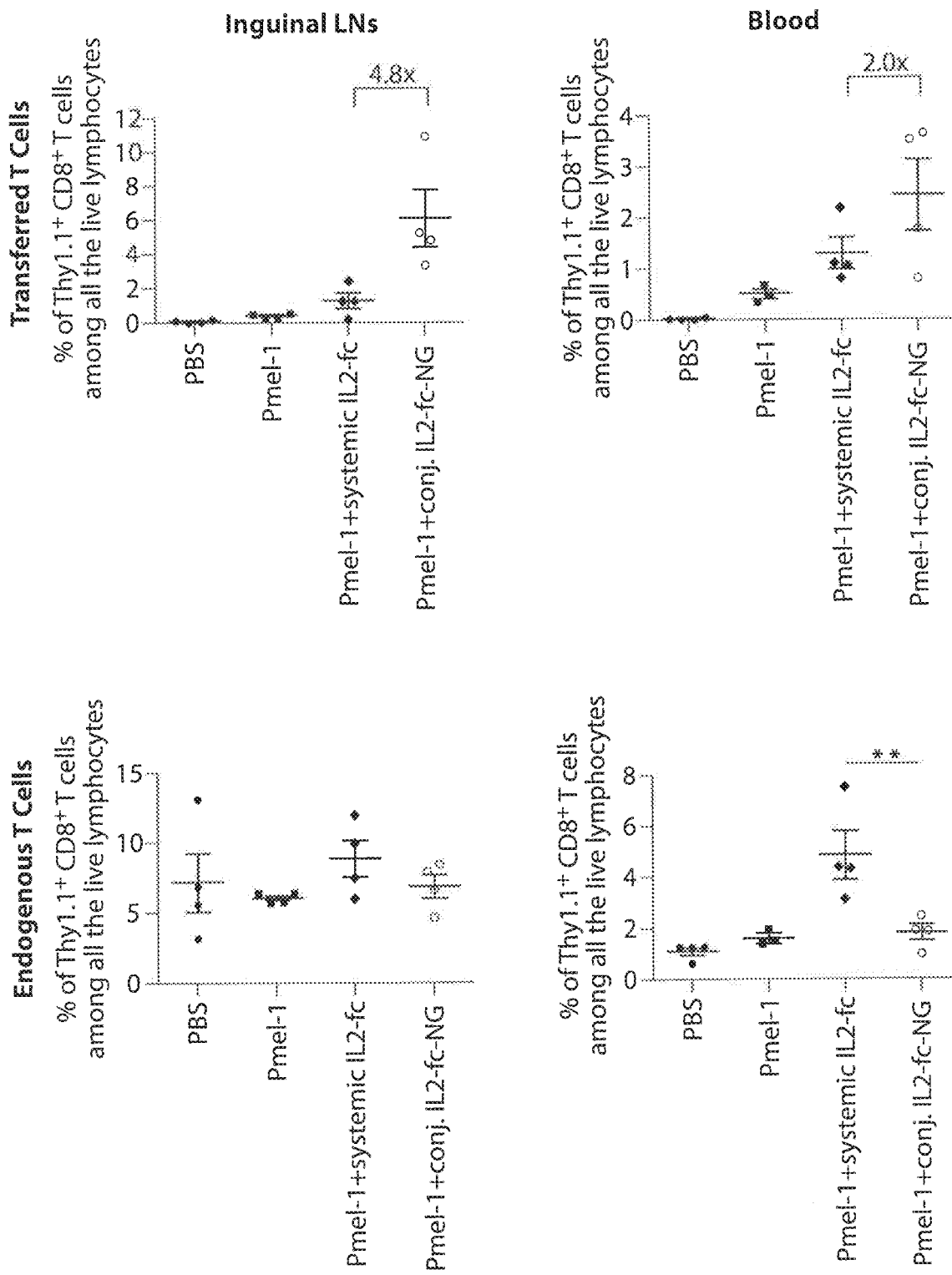
FIG. 16 show the frequency of adoptively-transferred T cells and endogenous T cells in the inguinal lymph nodes (left) and blood (right) analyzed with flow cytometry 12 days (Day 12) after adoptive transfer.

The frequency of adoptively-transferred T cells and endogenous T cells in the inguinal lymph nodes and blood were analyzed with flow cytometry on Day 12 after adoptive transfer. By comparing with the group of Pmel-1$^+$ systemic IL2-Fc, the T cells with conjugated IL2-Fc-crosslinked nanogels showed 4.8 and 2.0 fold increased frequency of transferred $CD8^+$ T-cells in LN and blood respectively. However, the systemic IL2-Fc expanded the endogenous $CD8^+$ T-cells nonspecifically in both the inguinal lymph nodes and blood (FIG. 16).

Figure 17A:
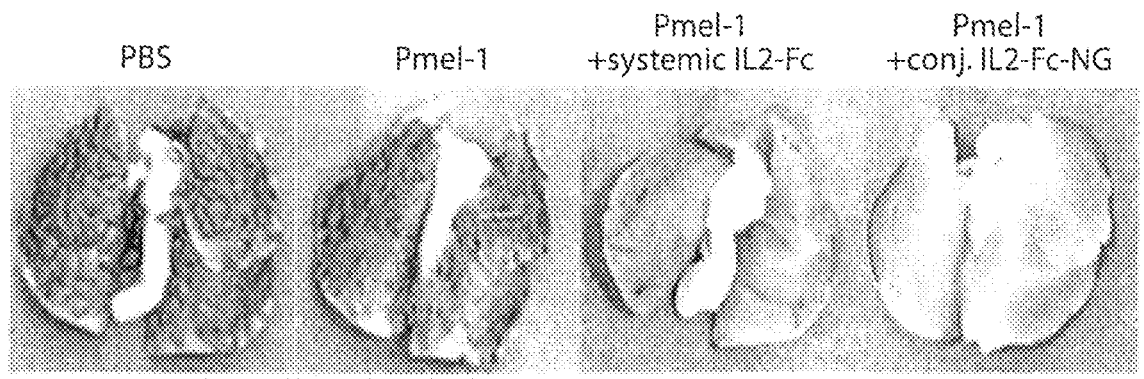
Figure 17B:
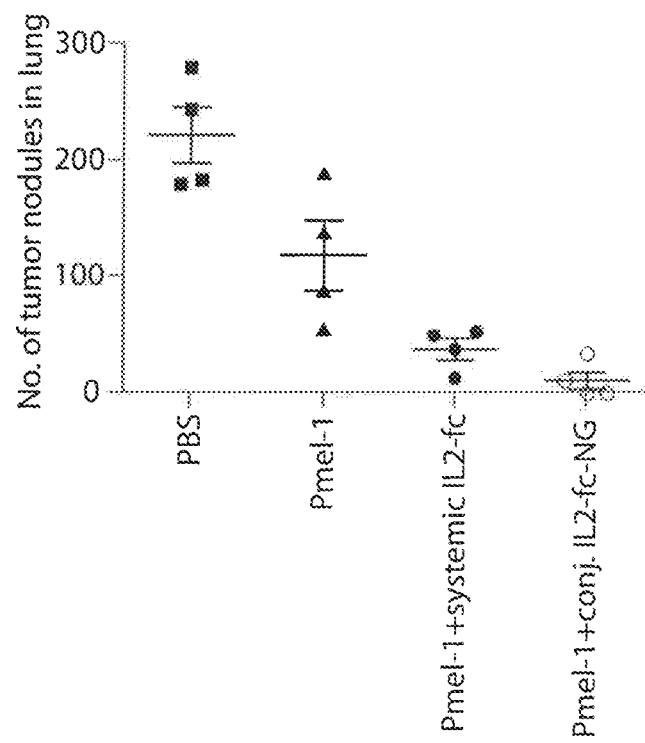

To evaluate the efficacy of the treatment of adoptive cell transfer, all the lungs were collected. By counting the number of tumor nodules in lung, it was shown that the mice treated with T cells having conjugated IL2-Fc-crosslinked nanogels had the lowest number of tumors (FIGS. 17A-17B), indicating that the specific expansion of adoptively-transferred T cells by conjugated IL2-Fc-crosslinked nanogels resulted in improved efficacy against the lung metastases of B16F10 melanoma. The efficacy results were further confirmed with histological analyses, and the mice treated with T cells with conjugated IL2-Fc-crosslinked nanogels also had the lowest grade of lung tumor burden (FIGS. 17C-17D).

T cell surface bound IL2-Fc-crosslinked nanogels provided long-lasting, specific expansion of adoptively-transferred T cells through sustained release of intact IL2-Fc in vivo and, thus, improved the efficacy of adoptive T cell therapy against cancer.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

It should also be understood that, unless clearly indicated to the contrary, in any methods claimed herein that include more than one step or act, the order of the steps or acts of the method is not necessarily limited to the order in which the steps or acts of the method are recited.

All references (e.g., published journal articles, books, etc.), patents and patent applications disclosed herein are incorporated by reference with respect to the subject matter for which each is cited, which, in some cases, may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nanostructure comprising a plurality of immunostimulatory proteins reversibly crosslinked to each other through a degradable linker that degrades under physiological conditions to release the immunostimulatory proteins, wherein the immunostimulatory proteins are immunostimulatory cytokines, antigens, or immunostimulatory antibodies or antibody fragments.

2. The nanostructure of claim 1, wherein the immunostimulatory proteins are immunostimulatory cytokines.

3. The nanostructure of claim 2, wherein the immunostimulatory cytokines are IL-2, IL-7, IL-15, IL-15 superagonist, IFN-gamma, IFN-alpha, GM-CSF, or FLT3-ligand.

4. The nanostructure of claim 2, wherein the immunostimulatory cytokines are IL-15 or IL-15 superagonist.

5. The nanostructure of claim 1, wherein the immunostimulatory proteins are fusion proteins.

6. The nanostructure of claim 1, further comprising a polymer.

7. The nanostructure of claim 6, wherein the polymer is surface conjugated to the nanostructure.

8. The nanostructure of claim 7, wherein the polymer is covalently conjugated.

9. The nanostructure of claim 7, wherein the polymer is non- covalently conjugated.

10. The nanostructure of claim 6, wherein the polymer comprises poly(ethylene oxide), polylactic acid, poly(lactic-co-glycolic acid), polyethylene glycol, polyglutamate, or polylysine.

11. The nanostructure of claim 1, wherein the nanostructure is conjugated to the surface of a carrier cell.

12. The nanostructure of claim 11, wherein the carrier cell is an engineered carrier cell.

13. The nanostructure of claim 11, wherein the carrier cell is lymphocyte.

14. The nanostructure of claim 13, wherein the lymphocyte is an NK cell, a B cells, a T cell, a CD4+T cell, a CD8+T cell, a cytotoxic T cell, or a NK T cell.

15. The nanostructure of claim 14, wherein the lymphocyte is genetically engineered.

16. The nanostructure of claim 13, wherein the lymphocyte is specific to a tumor antigen.

17. The nanostructure of claim 11, wherein the nanostructure is noncovalently conjugated to the surface of the carrier cell.

18. A composition comprising a plurality of nanostructures, each nanostructure comprising a plurality of immunostimulatory proteins reversibly crosslinked to each other through a degradable linker that degrades under physiological conditions to release the immunostimulatory proteins, wherein the immunostimulatory proteins are immunostimulatory cytokines, antigens, or immunostimulatory antibodies or antibody fragments.

19. The composition of claim 18, wherein the immunostimulatory proteins are immunostimulatory cytokine.

20. The composition of claim 19, wherein the immunostimulatory cytokines are IL-2, IL-7, IL-15, IL-15 superagonist, IL-12, IFN-gamma, IFN-alpha, GM-CSF, or FLT3-ligand.

21. The composition of claim 19, wherein the immunostimulatory cytokines are IL-15 or IL-15 superagonist.

22. The composition of claim 18, wherein the immunostimulatory proteins are fusion proteins.

23. The composition of claim 18, further comprising a polymer.

24. The composition of claim 23, wherein the polymer is surface conjugated to the nanostructure.

25. The composition of claim 24, wherein the polymer is covalently conjugated.

26. The composition of claim 24, wherein the polymer is non- covalently conjugated.

27. The composition of claim 23, wherein the polymer comprises poly(ethylene oxide), polylactic acid, poly(lactic-co-glycolic acid), polyethylene glycol, polyglutamate, or polylysine.

28. The composition of claim 18, wherein the plurality of nanostructures are conjugated to the surface of a carrier cell.

29. The composition of claim 28, wherein the carrier cell is an engineered carrier cell.

30. The composition of claim 28, wherein the carrier cell is a lymphocyte.

31. The composition of claim 30, wherein the lymphocyte is an NK cell, a B cells, a T cell, a CD4+T cell, a CD8+T cell, a cytotoxic T cell, or a NK T cell.

32. The composition of claim 31, wherein the lymphocyte is genetically engineered.

33. The composition of claim 30, wherein the lymphocyte is specific to a tumor antigen.

34. The composition of claim 30, wherein the plurality of nanostructures are noncovalently conjugated to the surface of the carrier cell.

35. A method of treating a condition or a disease in a subject, comprising administering the nanostructure of claim 1.

36. The method of claim 35, wherein the condition or disease is cancer, diabetes, an autoimmune disease, or a cardiovascular disease.

37. The method of claim 35, wherein the nanostructure is administered by oral, intravenous, intraperitoneal, intramuscular, intracavity, intratumor, or transdermal route of administration.

38. A method of treating a condition or a disease in a subject, comprising administering the nanostructure of claim 18.

39. The method of claim 38, wherein the condition or disease is cancer, diabetes, an autoimmune disease, or a cardiovascular disease.

40. The method of claim 38, wherein the nanostructure is administered by oral, intravenous, intraperitoneal, intramuscular, intracavity, intratumor, or transdermal route of administration.

* * * * *